(12) United States Patent
Schaafsma

(10) Patent No.: US 7,794,403 B2
(45) Date of Patent: Sep. 14, 2010

(54) SYSTEM FOR MEASURING PULSATILE VASCULAR RESISTANCE

(75) Inventor: Arjen Schaafsma, Assen (NL)

(73) Assignee: MEAR Holding B.V., Assen (NL)

(*) Notice: Subject to any disclaimer, the term of this patent is extended or adjusted under 35 U.S.C. 154(b) by 913 days.

(21) Appl. No.: 11/587,021

(22) PCT Filed: Apr. 21, 2005

(86) PCT No.: PCT/NL2005/000297

§ 371 (c)(1),
(2), (4) Date: Dec. 11, 2006

(87) PCT Pub. No.: WO2005/102158

PCT Pub. Date: Nov. 3, 2005

(65) Prior Publication Data

US 2007/0293760 A1    Dec. 20, 2007

(30) Foreign Application Priority Data

Apr. 21, 2004  (EP) .................................. 04076210

(51) Int. Cl.
*A61B 5/00* (2006.01)
(52) U.S. Cl. .................... 600/485; 600/500; 600/504
(58) Field of Classification Search .................. None
See application file for complete search history.

(56) References Cited

U.S. PATENT DOCUMENTS

| 4,688,577 | A | 8/1987 | Bro |
| 4,807,638 | A | 2/1989 | Sramek |
| 5,579,774 | A | 12/1996 | Miller et al. |
| 5,743,268 | A | 4/1998 | Kabal et al. |
| 2004/0024324 | A1 | 2/2004 | Bratteli |

FOREIGN PATENT DOCUMENTS

DE    196 00 983 C    5/1997
EP    1 250 889 A     10/2002

*Primary Examiner*—Robert L Nasser
(74) *Attorney, Agent, or Firm*—Hoffmann & Baron, LLP

(57) ABSTRACT

The invention relates to acquiring information concerning the hemodynamic status of the brain (or any other organ) by measuring and analysing the pulsatile properties of blood flow (velocities) in the organ's feeding vessels in relation to the pulsatile properties of the systemic arterial blood pressure. Provided is a system for the analysis of arterial blood flow velocity measurements, comprising means for receiving input signals delivered by an arterial blood flow velocity (FV) sensor and by an arterial blood pressure (BP) sensor, wherein said FV and BP signals are recorded simulataneously and continuously, further comprising means for processing and outputting signals, wherein said processing comprises calculating the pulsatile apparent resistance (PaR) or the Pulse Flow Velocity Mismatch (PFVM). Plotting PAR or PVFM against mean arterial blood pressure and/or end tidal $CO_2$ levels can serve as an indicator for the effectiveness of imposed therapy.

17 Claims, 23 Drawing Sheets

SYSTEM FOR MEASURING PULSATILE VASCULAR RESISTANCE

This application is the U.S. National Phase of, and Applicant claims priority from, International Application Number PCT/NL2005/000297 filed 21 Apr. 2005 and European Patent Application bearing Serial No. EP 04076210.6 filed 21 Apr. 2004 which are incorporated herein by reference.

BACKGROUND OF THE INVENTION

The invention relates to the field of acquiring and analysing biological signals, more specifically signals representing blood flow velocity and blood pressure. The invention will be described with reference to the problem of acquiring information concerning the physiological status of the brain from the measurement and analysis of blood flow velocities in the brain arteries and systemic blood pressure. However, the invention may also be used to acquire information concerning the physiological status of (blood flow velocity and blood pressure in) other body parts or organs.

Each time the heart beats, it forces blood out into the arteries of the body. A portion of this blood enters the skull through the carotid arteries to supply oxygen and nutrients to the brain. The pumping of the blood by the heart creates a pulsation of the blood through the arteries. This pulsation of the blood in the arteries of the brain contributes to the fluid pressure levels in the brain. The high level of brain metabolism requires a constant supply of oxygen and nutrients regardless of possible shifts in systemic blood pressure occurring due to variations in heart rhythm or respiratory function. The flow of blood to the brain is automatically regulated by the body to avoid cerebral hypo- or hyperperfusion. Furthermore, the body maintains arterial blood pressure within safe limits, on the one hand maintaining adequate pressure levels for cerebral perfusion, on the other preventing high pressure levels to reach into the cerebral capillaries with a risk of fluid leakage or haemorrhage. Finally, other regulatory processes in the body operate to keep the level of the intracranial pressure within safe limits. Some of these other regulatory processes include the formation and absorption of cerebro-spinal fluid, maintenance of carbon dioxide levels in the blood, etc. When the brain is subjected to head trauma, internal bleeding, brain tumors or other abnormal conditions, the intracranial pressure may rise to dangerous levels impeding cerebral perfusion. If the body's regulatory processes are not able to control the increased intracranial pressure, then death may result.

In 1982, transcranial Doppler ultrasound (TCD) was introduced, a non-invasive technique for the measurement of flow velocities in intracranial arteries by means of ultrasound signals transmitted through bone (see for example Peters P, Datta K: Middle cerebral artery blood flow velocity studied during quiet breathing, reflects hypercapnic breathing in man. In: Modelling and control of ventilation, Semple S J G, Adams L and Whipp B J (eds). Plenum Press New York 1995; 293-295). TCD has since been used for a great number of medical indications, amongst which the measurement of vasospasm in subarachnoid hemorrhage, the monitoring of intracranial flow velocities during carotid endarterectomy (CEA), the determination of collateral flow over the circle of Willis, the investigation of cerebral autoregulation, etc. CEA is a surgical procedure in which fatty deposits are removed from one of the carotid arteries. Carotid artery problems become more common as people age. The disease process that causes the formation of fat and other material on the artery walls is called atherosclerosis, popularly known as "hardening of the arteries." The fatty deposit is called plaque; the narrowing of the artery is called stenosis. The degree of stenosis is usually expressed as a percentage of the normal vessel diameter at the site of measurement.

TCD technology allows to analyse blood flow velocity with a high temporal resolution, which makes it a much more attractive method for bedside monitoring compared to other diagnostic brain imaging techniques such as FMRI (functional magnetic resonance imaging) or PET (positron emission tomography) analysis.

Although TCD is an elegant diagnostic tool as well as a convenient monitoring procedure, its widespread use has been hampered by the often difficult interpretation of the signal. For instance, when interpreting flow velocity measurements over the middle cerebral artery (MCA), often several confounding factors need to be taken into account, such as the angle of insonation (usually unknown in TCD); fluctuations in heart beat frequency; condition of the carotid arteries and/or possible changes in MCA vessel diameter; cerebrovascular resistance (CVR); respiratory function (blood level of carbon dioxide); the arterial blood pressure (ABP); the intracranial pressure (ICP); variations in anatomy of the circle of Willis; mental status and turbulence due to blood flow derived from collateral vessels such as, for instance, the anterior communicating artery.

Together, the factors mentioned above give rise to a considerable inter- and intra-individual variation in flow velocity measurement. Thus, to improve the relevance of TCD-monitoring, a reliable interpretation of the TCD signal is required.

SUMMARY OF THE INVENTION

The present invention now provides the insight that the diagnostic value of TCD monitoring is dramatically increased if the changes in blood flow velocity are related to changes in the systemic blood pressure. The invention relates to acquiring information concerning the hemodynamic status of the brain (or any other organ) by measuring and analysing the pulsatile properties of blood flow (velocities) in the brain's (or any other organ's) feeding vessels in relation to the pulsatile properties of the systemic arterial blood pressure.

Provided is a system for the analysis of arterial blood flow velocity measurements, comprising means for receiving input signals delivered by an arterial blood flow velocity (FV) sensor and by an arterial blood pressure (BP) sensor, wherein said FV and BP signals are recorded simultaneously and continuously, further comprising means for processing and outputting signals, wherein said processing comprises calculating the pulsatile apparent resistance (PaR) or the Pulse Flow Velocity Mismatch (PFVM). Both parameters express in different ways the mismatch between the actual pulsatile properties of the brain's (or any other organ's) feeding vessels and the pulsatile properties of the BP signal. This mismatch is thought to arise from a pulsatile vascular resistance causing a decrease in the vessel's diameter during systole, resulting in a relative increase in blood flow velocity, and an increase in the vessel's diameter during diastole, resulting in a relative decrease in blood flow velocity. Pulsatile vasoconstriction is only possible when a vessel is not maximally vasoconstricted or, alternatively, maximally vasodilated. Thereby, the presence of pulsatile vasoconstriction indicates that the vessel functions within the autoregulative region. Absence of pulsatile vasoconstriction indicates that the vessel has left the autoregulative interval, either at the lower limit (e.g. during hypotension or $CO_2$ retention) or at the upper limit (e.g. during hypertension or $CO_2$ reduction). Consequently, plotting PaR or PFVM against mean arterial blood pressure and/or end tidal $CO_2$ levels can serve as an indicator for the effectiveness of imposed therapy. Also provided is a method for determining PaR and/or PFVM and an apparatus carrying out such a method.

DESCRIPTION OF THE INVENTION

Although the techniques used in this study are also applicable to other arteries, this description focuses on flow signals derived from the middle cerebral artery (MCA). Apart from the fact that this artery transports blood to roughly two thirds of the cerebral hemisphere it is important to realise that this artery only transports blood to cerebral tissue, whereas other vessels conventionally studied with TCD, such as the P1 or A1 segments, are also entailed in the redistribution of blood over the circle of Willis.

It is fundamental to the interpretation of TCD that the signal provides flow velocity (FV; in cm/s) and not flow (F; in $cm^3/s$) as provided by SPECT or PET scanning. If we could use a measurement of flow, the following would hold:

$$ABP = F.CVR \tag{1}$$

and therefore, $$CVR = ABP/F \tag{2}$$

Consequently, an increase in F indicates a decrease in CVR and a decrease in F indicates an increase in CVR.

Flow can be calculated from flow velocity if the vessel's cross-sectional area (A) and the angle of insonation ($\alpha$) is known:

$$FV = F/(A.\cos \alpha)$$

Of course, in this formula FV should denote the median Flow Velocity measured and not the maximum Flow Velocity (as defined by the so-called envelope of the TCD signal). However, because we will not attempt to measure actual Flow when comparing ABP and TCD, we will use FV in the sense of maximal FV, since this signal is more conveniently derived from the TCD apparatus.

Now flow velocity is often taken proportional to flow. Implicitly this assumes that A and $\cos \alpha$ are constant. The latter is of course the case as long as the TCD probe is not moved. The first is not as trivial as one may assume. The average diameter of the vessel will be roughly constant when one considers a prolonged period of time, for instance over a period of 10 to 20 heartbeats in succession. For such a prolonged period of time formula (2) may be rewritten as:

$$mCVR = c.mABP/mFV \tag{4}$$

wherein $$c = A.\cos \alpha \tag{5}$$

In formula (4) the "m" denotes the long term mean of either cerebro-vascular resistance, ABP or FV, in order to emphasise that this formula is only acceptable when analysing a number of heart beats in succession. Indeed, we shall see that formula (4) does not provide satisfactory explanation for the fluctuations in CVR within a single heartbeat. For this, we have to realise that within one heartbeat the vessel's diameter A cannot be assumed constant. Smooth muscle layers in the MCA vessel wall can contract and thereby cause a pulsatile variation of A.

If the ABP and FV signals were synchronised in time, the following would hold for any moment of time $$aCVR = ABP/(A.\cos \alpha.FV) \tag{6}$$

In (6) we define aCVR as the apparent CVR, in recognition of the fact that the apparent CVR is not the true CVR but is at least partially influenced by the pulsatile variation of the vessel's diameter assuming that the angle of insonation $\alpha$ remains the same.

Now, we assume that the average aCVR over the length of one heartbeat is equal to the mCVR calculated from (4). In order to eliminate respiratory fluctuation in mCVR it is wise to average mCVR over the former 10 or 20 heart cycles. aCVR can now be seen as varying in a pulsatile fashion around mCVR. If the cross-sectional area is small (during systole), the flow velocities will be relatively high and, therefore, the apparent CVR will be smaller than mCVR. When the cross-sectional area is relatively large (during diastole), the flow velocities will be relatively low and the apparent CVR will be larger than the mCVR. The pulsatile variation in aCVR, therefore, corresponds to the MCA cross-sectional area. Theoretically, this variation in cross-sectional area will be decreased or absent at either maximal vaso-dilatation of vaso-constriction. Therefore, the limits of cerebral autoregulation are reached when there is no pulsatile variation in aCVR. This consideration is the basis of an important indicator of cerebral autoregulation: the pulsatile apparent cerebrovascular resistance or puls_aCVR or, when other organs than the brain are considered, the pulsatile apparent resistance or PaR.

Firstly, we subdivide one heart beat in a systolic part defined by any interval between pulse onset and the so-called incisure within the ABP or FV-signals, indicating the closing of the aortic valves. Then we define a diastolic part as an interval of fixed duration (and thus independent of heart beat frequency) after the incisure and directly preceding the next pulse onset. For the systolic part we can write $$sys\_aCVR = sys\_ABP/sys\_FV \tag{7}$$

Likewise for the diastolic part we can write $$dias\_aCVR = dias\_ABP/dias\_FV \tag{8}$$

sys_ABP, sys_FV, dias_ABP and dias_FV are the average values for ABP and FV over the systolic or diastolic part within each heart cycle.

Then, it is of interest to define the pulsatile apparent resistance or $$PaR = (dias\_aCVR - sys\_aCVR)/mCVR \tag{9}$$

The pulsatile apparent resistance is expressed as a percentage of mCVR. If the vessel is maximally constricted the PaR will drop to 0 at high values of mCVR. If the vessel is maximally dilated the PaR will drop to 0 at low values of mCVR. In between, the PaR will normally have a positive value since the apparent CVR during diastole will be larger than during systole. PaR is independent on the angle of insonation, since it's value is calculated relative to mCVR. MCVR itself, on the contrary, will differ from individual to individual since it depends on the position and direction of the TCD probes which can vary from study to study.

PaR is a stable parameter that can be compared from one individual to another. Therefore, it can be plotted (1) as a function of mean arterial blood pressure (mABP) and (2) as a function of end tidal $CO_2$ ($ETCO_2$) measured from a subject's exhalation gas by capnography. MABP and $ETCO_2$ are the two most important factors influencing cerebral perfusion. Both factors are easily influenced by therapeutic measures taken by the responsible clinician, for instance changing mABP by infusion of fluid expanders or cardio-vascular drugs or changing $ETCO_2$ by adjusting the parameters of a breathing apparatus. Expressing PaR as a function of both factors can provide instantaneous feedback to the clinician how successful the therapeutic intervention is with respect to returning intracranial hemodynamic state within the boundaries of cerebral autoregulation.

Although several assumptions and simplifications underlie the definition of PaR its usefulness in clinical practice can easily be illustrated.

Theoretically, there are some other ways of expressing the variability in aCVR. It is also possible to consider the variation within one heart beat by analysing the signal after normalisation, setting the minimal diastolic flow velocity and blood pressure prior to stroke onset at 0 and the maximal systolic flow velocity and blood pressure at 1. This technique filters away low frequency changes in mCVR since minimal and maximal values for FV and ABP are recalculated for every heart beat. It leads to a norm_FV and a norm_ABP signal. Over one heart cycle one can calculate the average norm_aCVR relative to the norm_aCVR during systole, which was set at 1. This is named the pulse flow velocity mismatch (PFVM):

$$PFVM = \text{mean\_norm\_}ABP/\text{mean\_norm\_}FV \quad (10)$$

Superimposing the normalised ABP and TCD signals can nicely demonstrate that there is a mismatch between the ABP and TCD signal. The PFVM is a numerical expression of this mismatch. After testing the different parameters proposed it seems that PaR in particular is most informative about the cerebral autoregulative state.

Thus, further provided is a system for the analysis of arterial blood flow velocity measurements comprising means for receiving input signals delivered by an arterial blood flow velocity (FV) sensor and by an arterial blood pressure (BP) sensor, wherein said FV and BP signals are recorded simultaneously and continuously, further comprising means for processing and outputting signals, wherein said processing comprises (i) normalizing said FV and BP signal with the minimal diastolic flow velocity or blood pressure set at 0 and the maximal systolic flow velocity or blood pressure set at 1; (ii) optionally synchronizing the normalized FV and the normalized BP signals at start-upstroke; (iii) calculating the mean normalized FV and the mean normalized BP per time unit; and (iv) determining the ratio between the mean normalized FV signal and the mean normalized BP signal.

The ratio between the mean normalized FV signal and the mean normalized BP signal provides another parameter that is reflective of the pulsatile vascular resistance. In this single parameter, herein further referred to as Pulse Flow Velocity Mismatch (PFVM), various aspects of both the continuous registration of FV as well as BP are combined. The PFVM can be provided real-time, is easy to interpret, robust, reproducible and sensitive to various changes in physiology.

A system of the invention comprises means for receiving signals delivered by an FV sensor and by a BP sensor, wherein said FV and BP signals are recorded simultaneously and continuously. In a preferred embodiment, the arterial blood flow velocity (FV) sensor of a system according to the invention detects the middle cerebral artery (MCA) flow velocity. This allows to acquire information concerning the physiological status of the brain of a subject, for example in a subject that has undergone surgery of the carotid artery. However, as said above, the invention is not limited to analysing intracranial signals and a system as provided herein is suitably used to analyse and interpret FV and BP signals acquired from other body parts or organs, e.g. a limb.

The continuous FV signal can be recorded using conventional medical Doppler ultrasound technology, either in a direct or indirect (non-invasive) fashion. For continuous flow measurements other techniques are available such as flow meters and indwelling probes which can be positioned around the aorta (or other blood vessels) for a direct determination of flow rates. This method is capable of giving highly accurate absolute flow rates (i.e. flow rates are reported in mL/min etc) and is very suitable for continuous readings. Small transducer tipped catheter probes can also be used, for example to monitor coronary arterial flow velocity (in cm/s). In a preferred embodiment, the FV of the middle cerebral artery (MCA-FV) is measured using TCD.

In another embodiment, an FV signal from a body part or organ other than the brain is recorded using a system of the invention that receives a signal from a flow velocity measurement system, e.g. a Laser Doppler system, which usually employs a fibre optic probe to apply light to a small area of tissue (non-invasive skin measurements are possible). The light is scattered by the tissue (usually a tissue volume of only a cubic millimetre or so around the probe tip is involved) and a small amount of this light re-enters the optic fibre to be recorded. The direction and rate of blood flow in the very small capillaries in the tissue cause a Doppler shift in the returned light, and it is this shift which constitutes the signal. The absolute strength of the signal is related to several factors including the degree of vascularisation of the tissue (i.e. how many and what size of blood vessels are in the tissue sample around the probe tip). Thus, the signal strength can vary markedly with position of the tip, and the tissue type (more heavily vascularised tissue works best). Also, a Laser Doppler sensor can detect changes in the very smallest blood vessels where most other techniques are of little use. In a further embodiment, Doppler ultrasound technology is used to record the flow velocity within other body parts or organs, for example the blood flow velocity in a leg artery.

The BP signal can be continuously recorded using an invasive or a non-invasive blood pressure sensor. Invasive sensors include an intravascular catheter. It is however preferred to use a non-invasive BP sensor, for example a non-invasive continuous finger blood pressure monitor known under the tradenames Finapres™ or Portapres™.

A system of the invention further comprises means for processing simultaneously and continuously recorded FV and BP signals. These means typically comprise a sampling circuit and a calculator. Different inputs (e.g. BP and FV signals) can be connected to the sampling circuit such that a digital signal is supplied to a calculator that can carry out the desired processing operations. According to the invention, the processing includes the operations of normalization of BP and FV signals, calculating the mean normalized BP and FV signals, determining the ratio between the mean normalized signals, and optionally synchronizing normalized BP and FV signals. Processing can be performed and output following recording the signals or during recording, in a real-time situation.

For the calculation of the PaR from the recorded signals it is preferable that the processor is equipped with hardware and software that is able to 'translate' the analogous signals that have been recorded into digital signals and then to perform the above mentioned calculations on the signals. It is essential that the signals are synchronized before calculation to provide adequate results. Such a synchronisation should correct for any shifts in (one of) the signals resulting from the recording or preprocessing of the signal. Signals can be out of phase, for instance, because the BP is measured at one place of the body, while the FV is measured in another part of the body.

Preferably, the data is analysed under two testing conditions: a resting condition and a condition of deep breathing during which the subject is asked to perform deep inhalations and exhalations, each with a duration of at least 5 sec and for a total of 8 times in succession. Normally, a marked respiratory variation occurs in the heart frequency during deep breathing (as was the case in the cases reported in Example 7 and 8). Therefore, the variation in heart frequency should preferably be taken to calculate averaged signals for both the flow velocity and blood pressure per heart beat for different respiratory phases.

For this, the respiratory cycle can be subdivided into, for example, 8 phases, 4 during in and 4 during expiration. For each of these phases the data of 3 heart beats with similar BTB intervals can be combined and averaged to obtain a representative signal.

For the embodiment in which the PFVM is calculated, first the FV and BP signal are normalized with the minimal diastolic flow velocity or blood pressure set at 0 and the maximal systolic flow velocity or blood pressure set at 1. Second, the normalized FV and the normalized BP signals may be synchronized to take into account the time shift between both signals, since the FV signal may be derived from vessels (e.g. intracranial) which are closer to the heart than the artery from which the BP signal is derived (e.g. radial artery or finger artery). FIG. 1A displays examples of a normalized MCA-FV signal superimposed on a BP signal, wherein one of the signals is shifted in time (usually advancing the BP signal with 60-80 ms) for an optimal synchronization of FV and BP start-upstroke. In this case the synchronization of both signals was made easier by making use of a simultaneously recorded ECG signal. It is also possible to shift the FV signal in time or to synchronise the signals prior to normalization.

In the third operation, both the mean normalized pulsatile FV as well as BP are calculated within a chosen time-frame, e.g. the interval between two successive heart beats. Since the blood pressure difference over the middle cerebral artery is equal to the blood flow times the cerebrovascular resistance ($\Delta P = F \cdot CVR$) and the blood flow is equal to the blood flow velocity (as measured by TCD) multiplied by the vessel's diameter at the location of measurement ($F = FV \cdot A$) the CVR should roughly be proportional to $\Delta P/FV$, provided the A(rea) remains constant. This, of course, also holds for the pulsatile (high pass filtered) components in BP and MCA-FV signals. If the cerebrovascular resistance would be constant, the normalized pulsatile signals of MCA-FV and BP would coincide. This can for instance be found during profound hyperventilation as shown in FIG. 2. Normally however, the surface area under the curve of the normalized pulsatile signal of the MCA-FV is larger than that of the normalized pulsatile signal of BP as was already demonstrated in FIG. 1.

Following calculation of the mean normalized FV and BP signals, the ratio between the mean normalized FV signal and the mean normalized BP signal is calculated, to yield the aforementioned PFVM. In one embodiment, a system of the invention further comprises means for displaying the PFVM, for instance a screen. A system of the invention may also comprise a storage unit to store recorded signals and/or calculated PFVM values.

In one aspect of the invention, the FV and BP signals are normalized relative to the minimum and maximum signals obtained in the period in between two successive heart beats. For each heart beat, the mean normalized pulsatile FV and BP signals are calculated to yield for each heart beat a PFVM value (see FIG. 1C). The timing of the heart beat can be derived from the FV and/or BP signal. Preferably however, the heart rate is measured separately and the heart frequency is displayed in an electrocardiogram (ECG). In a further embodiment, the FV and BP signals are normalized relative to the signal recorded over a longer period, e.g. a period including one or two heart beats preceding and following a particular heart beat such that a 'running average' of three or five successive heart beats, respectively, is obtained. Generally speaking, normalization over a longer time unit results in a better signal-to-noise ratio. For real-time PFVM calculations, it is possible to calculate the mean normalized FV and BP signals using the minimum and maximum values obtained in one or more preceding heart beats.

In yet another embodiment, the PFVM value is calculated continuously instead of per heart beat (see FIG. 1B). To that end, the normalized FV ad BP signals are synchronized at start-upstroke.

As said the PFVM can be calculated for each heart beat from the ratio of the mean normalized pulsatile BP and the mean normalized pulsatile FV, for example the MCA-FV. Under normal conditions, the PFVM roughly ranges from 0.6 to 0.9. Larger values of the PFVM indicate a larger mean pulsatile CVR, smaller values of the PFVM indicate lower values. For instance, a PFVM equalling 1 indicates the optimal match of the normalized pulsatile ABP with the MCA-FV signal, a condition encountered for instance during general anaesthesia or profound hyperventilation. A PFVM smaller than 0.6 indicates a low pulsatile CVR, a condition encountered occasionally when cross-clamping the carotid artery during endarterectomy. Generally speaking, the CVR is not constant over the full duration of a heart beat, but has a pulsatile nature. This pulsatile CVR may arise from the smooth muscle layers in the intracranial arteries, which normally oppose stretch, and be under control of vaso-active substances, such as norepinephrine, acetylcholine and serotonin, released by nerve terminals within the vessel wall.

A system of the invention can be used to determine PFVM under various conditions, as is indicated in Examples 1 to 6. With respect to the calculation of PaR, Examples 7 and 8 show experimental evidence.

Since the PFVM is calculated from normalized pulsatile signals only, it is not influenced by for instance differences in calibration or differences in insonation angle. Thereby, the PFVM is a robust parameter. In addition, the interindividual variation in PFVM seems limited, roughly between 0.6 and 0.9 (arbitrary units). The PFVM seems to remain constant over a longer period of time, at least when no factors influencing the CVR are encountered (such as hyperventilation).

The invention further provides the use of a system of the invention as a diagnostic or (long term) monitoring device, for instance to diagnose or monitor a vascular disease or malfunction that is related to abnormal vascular resistance. In a specific embodiment, the invention provides a system for the diagnosis of a cerebrovascular disease or the risk of developing such a disease. The system is also very suitable for the diagnosis of elevated intracranial pressure affecting cerebral perfusion.

Furthermore, a system of the invention is advantageously used to monitor the physiological status of the brain of a subject following intracranial surgery or carotid endarterectomy (CEA). For instance, this may allow to assess the risk of developing a neurologic complication associated with CEA, including hypoperfusion during carotid clamping, perioperative carotid thrombosis and cerebral hyperperfusion syndrome (CHS). CHS is caused by insufficient cerebral autoregulation during the first days after CEA. Cerebral autoregulation may have become insufficient due to the fact that the brain arteries, for instance in bilateral carotid artery stenosis, have adapted to chronically low perfusion pressures. During carotid endarterectomy a stenosis is removed from an internal carotid artery and, consequently, the perfusion pressure is increased. In some patients the brain arteries have adapted to chronically low perfusion pressures and, after CEA, cannot build up sufficient resistance rapidly enough to oppose the abrupt increase in perfusion pressure. Of course, the development of CHS may further be enhanced by postoperative hypertension. Hyperperfusion syndrome associated with intracerebral haemorrhage is thought to account for approximately 10%-15% of all perioperative strokes.

In another embodiment of the invention, a method is provided for determining the pulsatile vascular resistance, preferably cerebrovascular resistance, said method comprising the steps of recording an arterial blood flow velocity (FV) signal and an arterial blood pressure (BP) signal, wherein said FV and BP signals are recorded simultaneously and continuously; normalizing said FV and BP signal with the minimal diastolic flow velocity or blood pressure set at 0 and the maximal systolic flow velocity or blood pressure set at 1; optionally synchronizing the normalized FV and the normalized BP signals at start-upstroke; calculating the mean normalized FV and the mean normalized BP over a given time period, for instance in between two successive heart beats; and determining the ratio between the mean normalized FV signal and the mean normalized BP signal, wherein the ratio is indicative of pulsatile vascular resistance during said given time period. Preferably, a method of the invention comprises real-time analysis of FV and BP signals. More preferably, in said method the FV of the middle cerebral artery is recorded (MCA-FV) such that a reliable diagnostic value is provided that reflects the pulsatile cerebrovascular resistance. Of course, a method of the invention is advantageously performed using a system as provided herein.

Also provided by the present invention is an apparatus for carrying out a method of the invention for determining the pulsatile (apparent) vascular resistance, PaR or PFVM. Preferably, said apparatus comprises a sensor for continuously recording an arterial blood flow velocity (FV) signal and a sensor for continuously recording an arterial blood pressure (BP) signal, the sensors being connected to means for receiving input signals, optionally further comprising a separate amplifier for FV and BP, which amplifiers generate signals which can be displayed on a display unit or recorded on a recording unit, said amplifiers both connected to a processor for performing signal analysis and calculation of the PaR or Pulse Flow Velocity Mismatch (PFVM), said amplifiers and said processor being connected to a display unit or a recording unit or both. In a specific embodiment, an apparatus of the invention comprises a transcranial Doppler ultrasound device and/or a non-invasive continuous finger blood pressure monitor, such as a Finapres™ or Portapres™ device.

The apparatus of the invention can be a stand-alone apparatus, which has the features as described above. It is also possible that the features are incorporated into a module, which can be coupled to or inserted in conventional devices, which are used in the same environment. It would be possible to plug such a module into a device, which is used for monitoring patients in a hospital or surgery environment, such as the above-mentioned transcranial Doppler ultrasound devices, blood-pressure meters, devices for the control and monitoring of anaesthesia, etc.

Graph of arterial blood pressure (ABP) and middle cerebral artery flow velocity (MCA-FV). Both signals have been normalized with the maximum systolic blood pressure and flow velocity set at 1 and the minimum diastolic blood pressure and flow velocity set at 0. Both signals have been synchronized with respect to start-upstroke which process was facilitated by making use of a simultaneously recorded ECG signal. The graph demonstrates a mismatch between the pulsatile blood pressure versus the middle cerebral artery flow velocity.

FIG. 1B

Figure 1A:
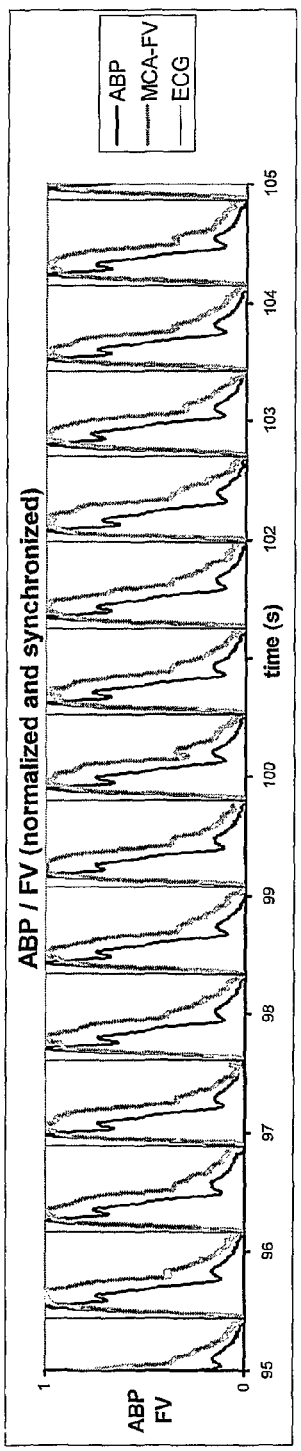
FIG. 1A

Graph of a continuous calculation of the pulsatile flow velocity mismatch (PFVM) by calculating the ratio of the normalized and synchronized ABP and FV signals from FIG. 1A per unit of time. This ratio gives an indication of vascular resistance (see text). The graph demonstrates that the vascular resistance is not constant over the period of one heart beat.

FIG. 1C

Graph of the calculated mean PFVM per heart beat. This is obtained by calculating the ratio of the mean normalized ABP signal (see FIG. 1A) divided by the mean normalized FV signal (see FIG. 1A) per heart beat (see text). In this way, a vascular resistance can be calculated relative to the vascular resistance at maximal systolic blood pressure. The graph demonstrates that the calculated mean PFVM varies over time, in this case with values between 0.6 and 0.7.

FIG. 2A

Same as in FIG. 1A, but now during hyperventilation. The graph demonstrates that the mismatch between the pulsatile blood pressure and the middle cerebral artery flow velocity is less than during normal breathing.

FIG. 2B

Figure 1B:
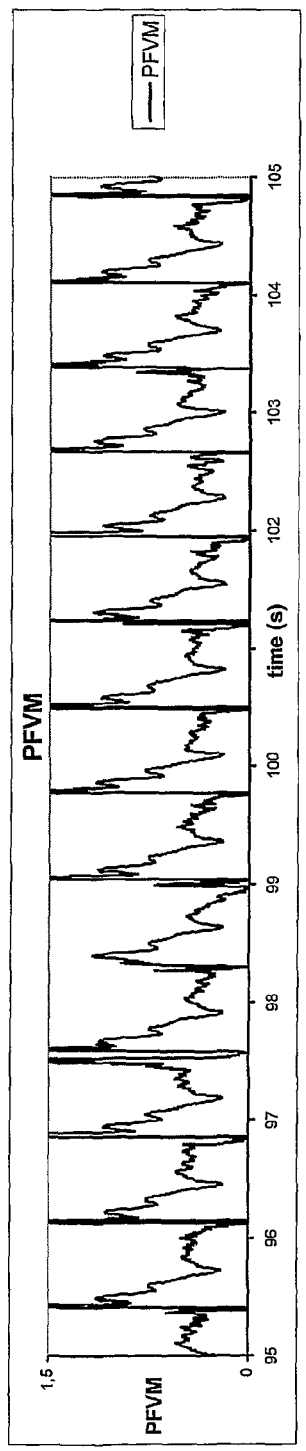

Same as in FIG. 1B, but now during hyperventilation. The graph demonstrates that the calculated PFVM approaches 1.0, since there is less variation in vascular resistance between systole and diastole.

FIG. 2C

Figure 1C:
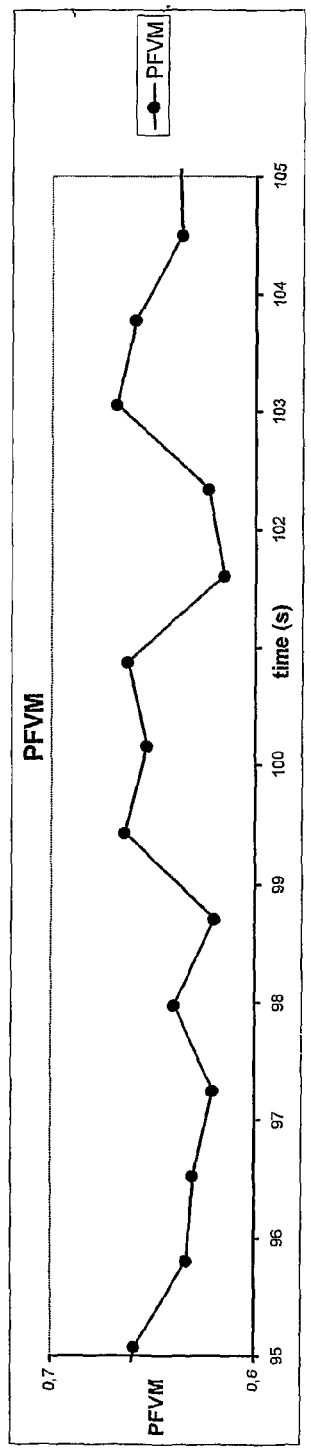
Figure 2A:
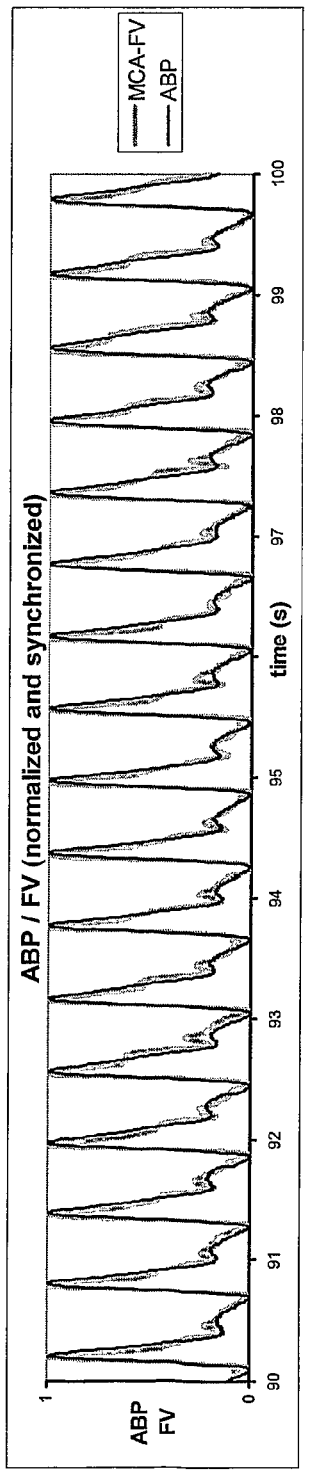
Figure 2B:
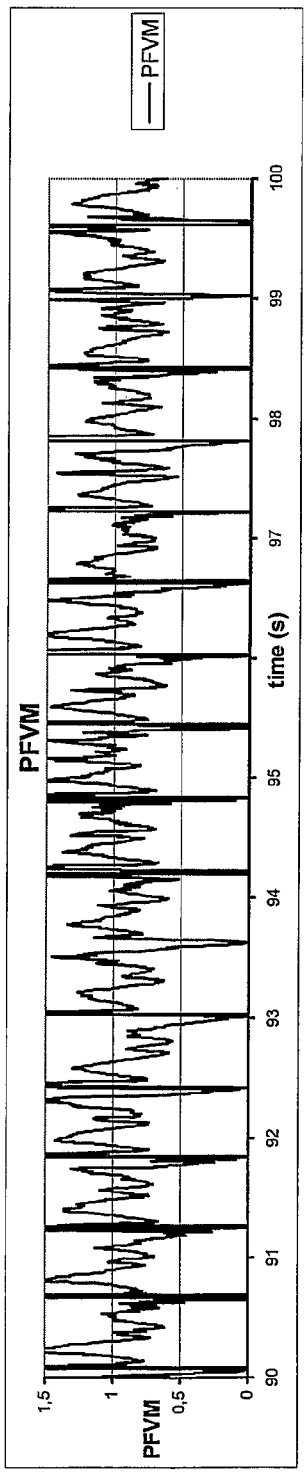
Figure 2C:
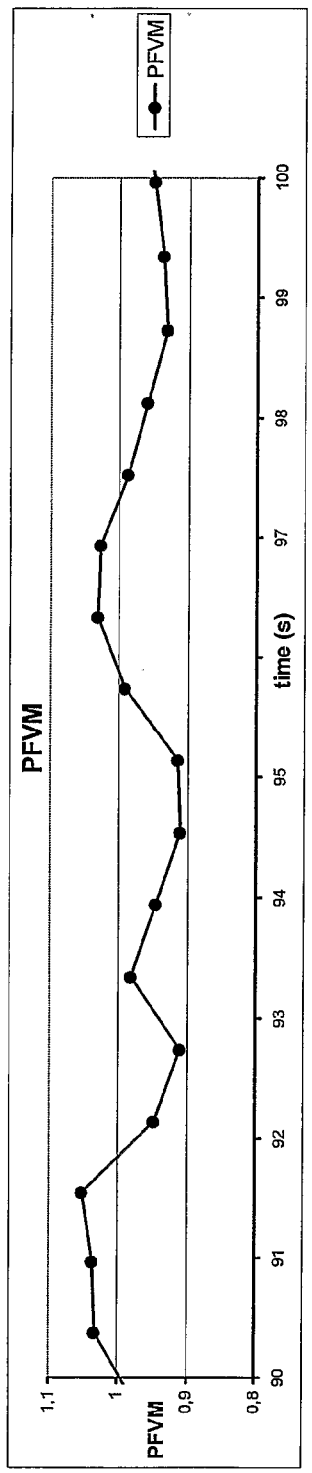

Same as in FIG. 1C, but now during hyperventilation. The graph demonstrates that the calculated mean PFVM now varies with values between 0.9 and 1.1.

FIG. 3A

Graph displaying the average values per heart beat of the mean arterial blood pressure (ABP; mmHg), the mean middle cerebral artery flow velocity (FV; cm/s) and the heart frequency (beats per minute) during deep breathing. Although there are large shifts in mean heart frequency and mean arterial blood pressure, the flow velocity over de middle cerebral artery varies only slightly.

FIG. 3B

Graph displaying the average values per heart beat of the normalized ABP and FV signals during deep breathing. The graph shows that these mean values display a complex, often biphasic, variation over time during deep breathing.

FIG. 3C

Graph displaying the mean calculated PFVM and the (scaled) heart frequency per heart beat during deep breathing. The graph shows that the PFVM varies in counter phase with the heart frequency: when the heart frequency goes up (indicating inspiration) the PFVM goes down and when the heart frequency goes down (indicating expiration) the PFVM goes up.

FIG. 4A

Figure 3A:
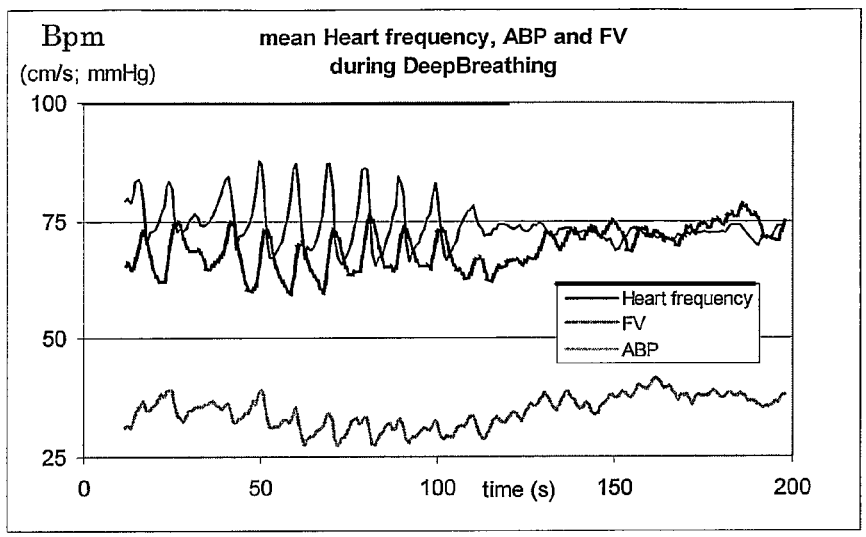

Same as in FIG. 3A, but now in a subject who was shown to have decreased $CO_2$ reactivity on the right side due to a hemodynamically significant stenosis of both internal carotid arteries. Again, deep breathing causes large shifts in arterial blood pressure and heart frequency. The graph demonstrates that on the right side larger fluctuations occur in middle cerebral artery flow velocity than on the left side.

FIG. 4B

Figure 3B:
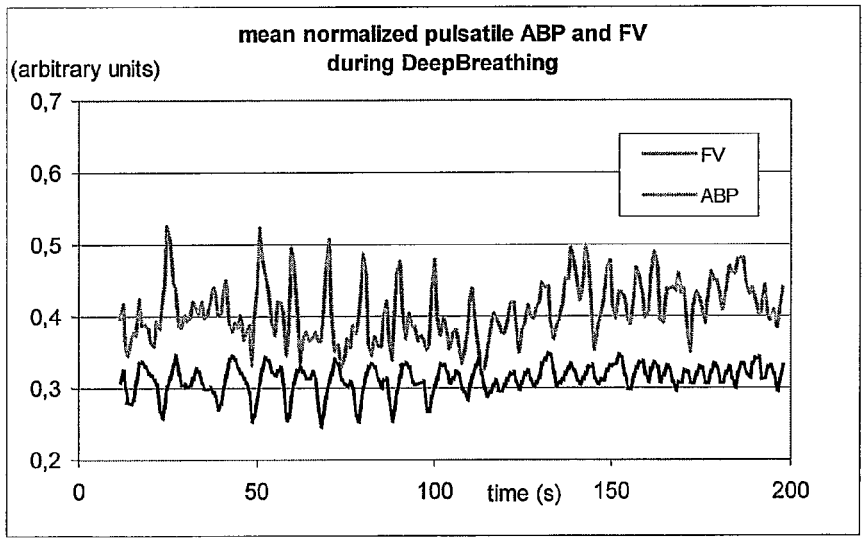
Figure 3C:
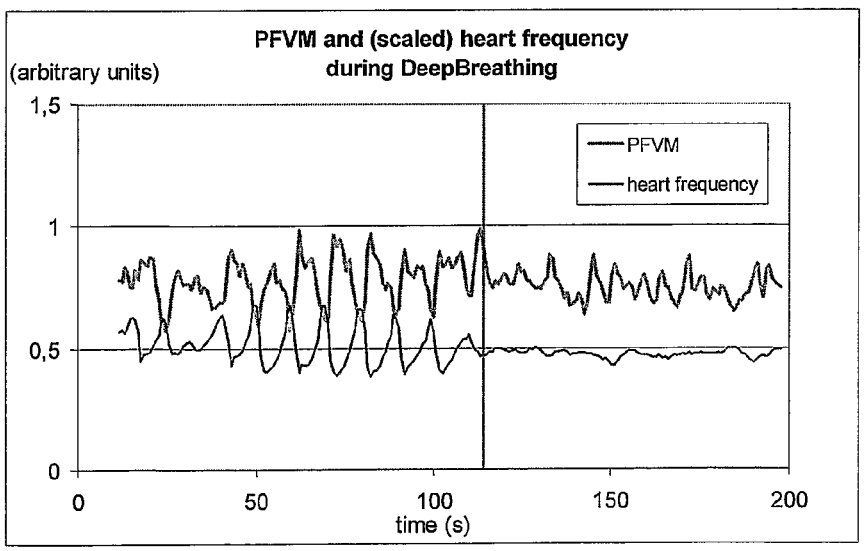

Same as in FIG. 3C, but now in a subject who was shown to have decreased $CO_2$ reactivity on the right side due to a hemodynamically significant stenosis of both internal carotid arteries. The graph demonstrates that on the right side no variation occurs in the PFVM, whereas the PFVM on the left side varies in counter phase with the heart frequency, as is normally seen.

FIG. 5A

Figure 4A:
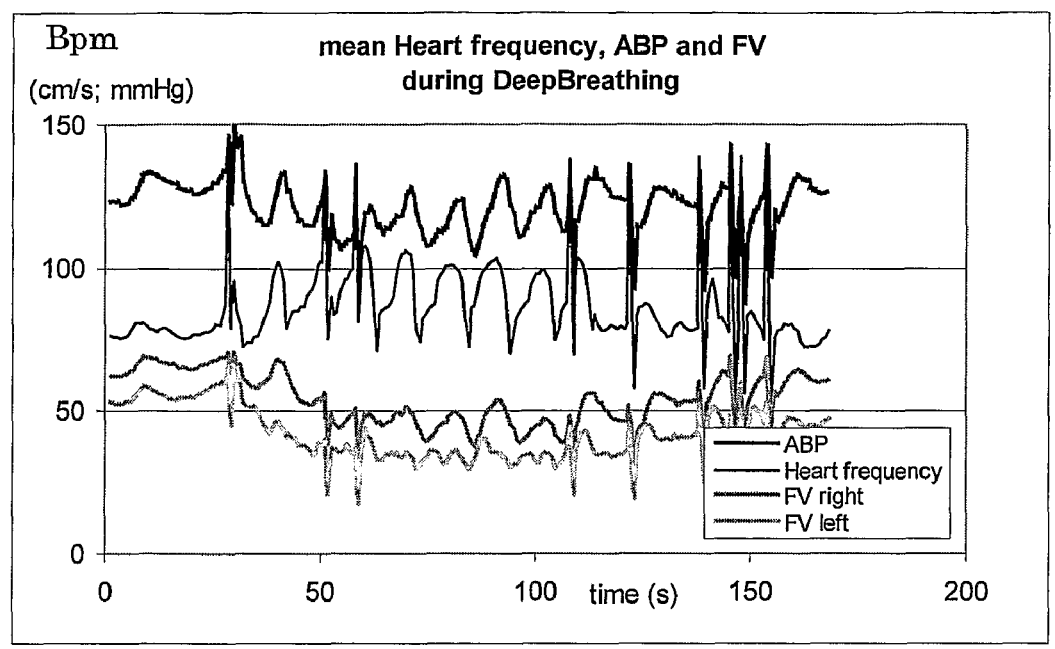

Same as in FIGS. 3A and 4A, but now while a subject is hyperventilating. During hyperventilation, the $CO_2$ level in the blood decreases. This causes a vasoconstriction in the brain arterioles. The mean middle cerebral artery flow velocity clearly decreases, while the heart frequency increases and while the mean arterial blood pressure remains roughly the same.

FIG. 5B

Graph displaying the mean calculated PFVM while a subject is hyperventilating. During hyperventilation the PFVM increases approaching 1. The value 1 indicates that the vascular resistance is constant over the full duration of a heart cycle or, in other words, there is no net pulsatile component in the vascular resistance.

FIG. 6A

Graph displaying the average of 5 successive tests during which a subject is asked to read a text silently and copy the text with the index finger of the right hand on the surface of the bed. Reading and writing with the right index finger are typically functions of the left cerebral hemisphere. The graph demonstrates that during this test a marked extra increase occurs in the middle cerebral artery flow velocity on the left side with respect to the right side (reading phase indicated on the x-axis from approximately 45 till 75 seconds). At rest both signals co-incide.

FIG. 6B

Figure 6A:
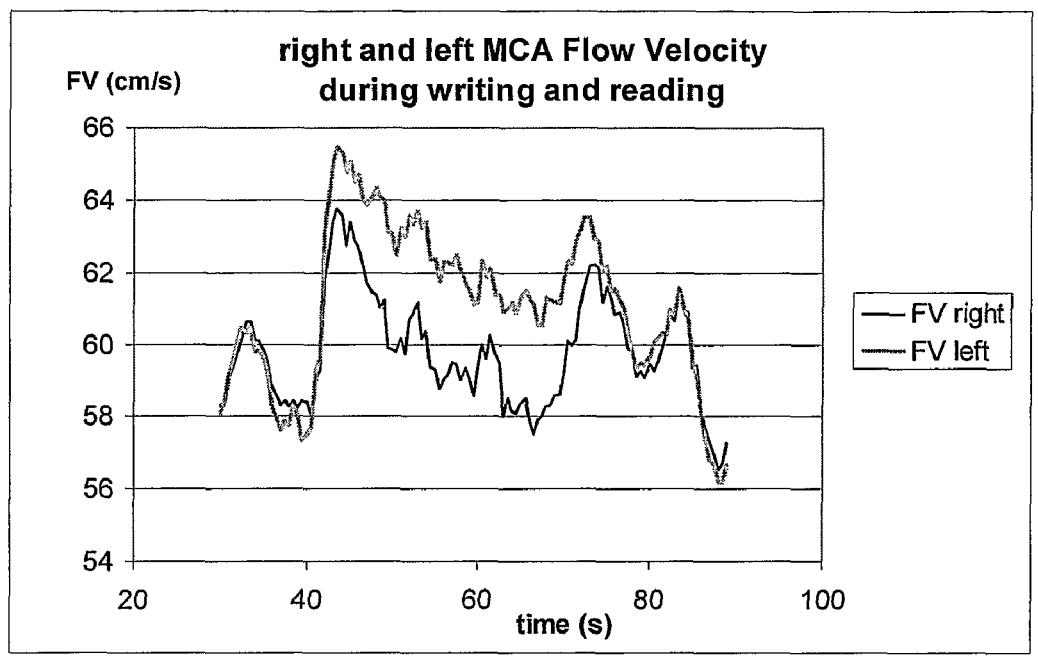

Graph displaying the average of 5 successive tests as described in FIG. 6A but now displaying the calculated values for the PFVM. The graph demonstrates that, although clear differences may be found in mean flow velocity over the left and right arteries, the PFVM for both sides remains roughly equal under these test conditions.

FIG. 7A

Same as in FIG. 1A, but now during general anaesthesia. The ABP signal is derived from a catheter placed in the radial artery instead of from a finger cuff procedure (Finapres™). The middle cerebral artery flow velocity is derived in exactly the same way as during other tests. The graph demonstrates that the mismatch between the pulsatile blood pressure and the middle cerebral artery flow velocity is less during general anaesthesia than when the subject is awake.

FIG. 7B

Same as in FIG. 1B, but now during general anaesthesia. The graph demonstrates that the calculated PFVM approaches 1.0 since there is less variation in vascular resistance between systole and diastole.

FIG. 7C

Same as in FIG. 1C, but now during general anaesthesia. The graph demonstrates that the calculated mean PFVM now fluctuates with values between 0.8 and 1.0.

FIG. 8.

Patient with a dissection of the internal carotid artery on the left side causing a subtotal stenosis. Calibrated ECG, maximal right and left MCA-FV and ABP signals: a.) subject supine at rest ventilating normally or b.) during deep breathing (5 seconds of deep inhalation followed by 5 seconds of deep expiration). Note the difference in flow velocity between both MCA's: right MCA-FV rapid upstroke with high frequency oscillation versus left MCA-FV blunted signal with slow upstroke. At rest both mean flow velocities are almost the same, whereas during deep breathing the flow velocities over the right MCA decrease while those over the left MCA do not change much. Also note time shifts between the QRS-complex of the ECG and the pulse waves of MCA-FV and ABP.

FIG. 9.

Figure 8A:
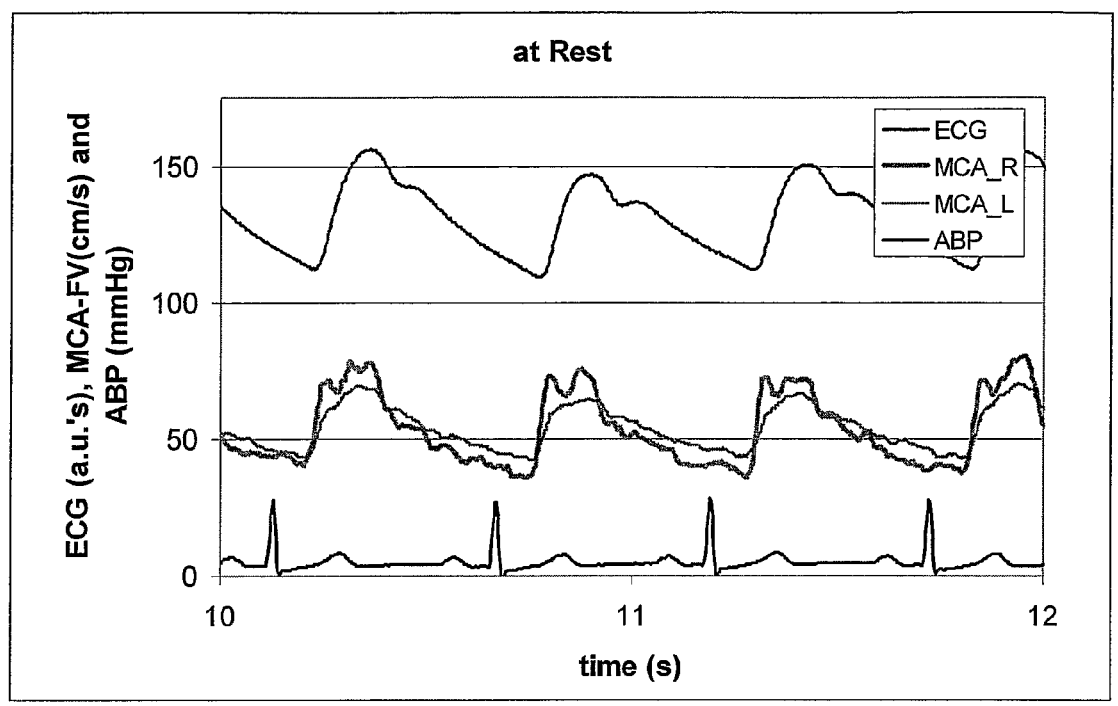
Figure 8B:
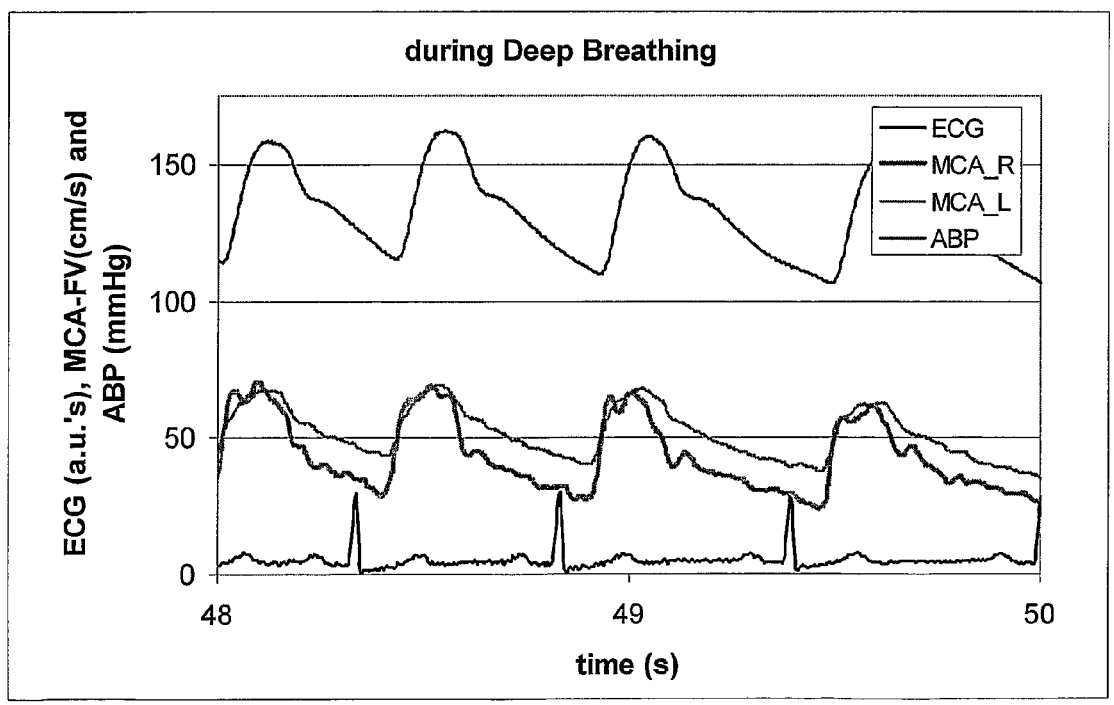

Beat-to-beat analysis of ABP (in mmHg), heart frequency (in BPM) and left and right MCA-FV (in cm/s) in the same patient as in FIG. 8: a.) subject supine at rest ventilating normally or b.) during deep breathing. Note increased mean arterial blood pressure secondary to left internal carotid artery dissection. Note respiratory fluctuations in ABP, HF and right MCA-FV signals which are less obvious in the left MCA-FV signal. Note low frequency changes in left MCA-FV signal which are present to a far lesser extent in the right MCA_FV signal. During deep breathing a large variation occurs in mABP and HF (respiratory arrhythmia) which are more or less dampened in the MCA-FV signals. Note drop in mean flow velocity of the right MCA (due to the lower blood $CO_2$ level) which does not occur in the left MCA.

FIG. 10.

Same patient as in FIG. 8. The (uncalibrated) right (a.) and left (b.) MCA-FV and (c.) ABP signals during deep breathing were selected based upon RR' intervals; each colored line represents the average over three heart beats with similar RR' intervals during inspiration or expiration in subsequent respiratory cycles. During inspiration the RR' intervals become shorter whereas during expiration they become longer. During inspiration the ABP increases, whereas during expiration the ABP decreases. This fluctuation in ABP is clearly visible during the systolic phase of the right MCA-FV signal but is almost absent during diastole. Apparently, the CVR is less adapted to variations in ABP during systole than during diastole. In the left MCA-FV signal the fluctuations in ABP are more clearly visible and the CVR seems overall less adaptive to ABP.

FIG. 11.

Same patient as in FIG. 8. After synchronization of the MCA-FV signals and the ABP with respect to the onset of upstroke the aCVR can be calculated by dividing the ABP through the MCA-FV signal (see text). This leads to a plot of the apparent CVR per respiratory phase. On the right side (a.) the variation in apparent CVR is much larger than on the left side (b.). The apparent CVR is lower during systole than during diastole because within 1 heart beat the effect of pulsatile variations in the cross-sectional area of the MCA cause an increase in flow velocity to correspond with an increase in CVR, whereas over longer periods of time (for instance, averaging data over 10-20 heart beats) an increase of flow velocity, on the contrary, corresponds with a decrease in CVR.

FIG. 12.

Same patient as in FIG. 8. The relation between MCA-FV and ABP is described by two models, the first model, calculating mCVR (a.), takes the flow velocity as an indicator of flow and is applicable when these signals are averaged over longer periods of time, the second model, calculating PaR (b.), takes the flow velocity as an indicator of changes in MCA cross-sectional area and is only applicable within one heart cycle. The outcome of both parameters is plotted for right and left MCA as a function of time. In a. the mCVR is calculated over a series of 10 successive heart beats. During deep breathing there is a larger increase in mCVR on the right than on the left side. This corresponds with the original data displayed in FIG. 9b. The PaR is larger on the right than on the left side indicating a larger pulsatile variation in MCA cross-sectional area corresponding with the findings in FIGS. 11a and b.

FIG. 13.

Combining the data of mABP and PaR into one graph for normoventilation and deep breathing. The data for normal ventilation are displayed by fat dots. On the right side the PaR is larger than on the left. Furthermore, there is a larger (respiratory) variation of the PaR on the right side than on the left. During deep breathing the variation in mABP is somewhat larger but for both sides the PaR remains within the same range.

FIG. 14.

Patient presenting with a status migrainosus. Note the large difference in ABP signal: during the status the ABP shows a much larger pulsatility than in the symptom free study. This larger pulsatility is also present in the MCA-FV signals which show a larger and steeper upstroke during the status than when the patient is symptom free.

FIG. 15.

Same patient as in FIG. 14 a.) during a status migrainosus and b.) during a symptom free period 2 weeks later. In a.) note the respiratory fluctuations of ABP which are also visible in the BTB-analyses of both MCA-FV. Note the small difference in mean FV between both MCA, the left slightly lower than the right. In b.) note the absence of major respiratory fluctuations in both the ABP and the MCA-FV signals. Note that the difference in FV between both MCA is either present or absent.

FIG. 16.

Same patient as in FIG. 14. The apparent CVR of the right MCA-FV calculated as described for FIG. 4 during the status migrainosus. Note that there is very little change in aCVR from systole to diastole. This indicates a loss of pulsatile variation in MCA cross-sectional area. Theoretically, this can either be due to maximal vaso-dilatation (vaso-paralysis) or maximal vaso-constriction (vaso-spasm).

FIG. 17.

Same patient as in FIG. 14 a.) during a status migrainosus and b.) during a symptom free period 2 weeks later. Plot of the PaR versus mABP at rest and during breathing. In a.) note the lowered PaR at high values for MABP, indicating maximal vaso-constriction. Furthermore, note that there is minimal change in mABP nor PaR during deep breathing despite a drop in $ETCO_2$ from 3.8 at rest to 2.8 during deep breathing. In b.) note that mABP is much lower allowing the PaR to become larger. During deep breathing there is an increase in mABP and a slight drop in PaR. This time the $pCO_2$ dropped from 4.7 at rest down to 4.2 during deep breathing. Comparing figures a) and b) suggests that cerebral autoregulation is essentially unchanged during the status migrainosus compared to when symptom-free.

FIG. 18.

Patient with right sided stenosis of the internal carotid artery with normal findings over the left side. Plots of color coded PaR as a function of mABP and $ETCO_2$ a.) on the right side and b.) on the left side. Each dot denotes the calculated PaR for a single heart beat. Total recording time is 40 minutes including a testing period of hyperventilation and a period with CO2 retention. Note that PaR on the right side is only normal (green dots) for a small number of combinations for mABP and $ETCO_2$, whereas on the left side a normal PaR is obtained for a much wider range of mABP and $ETCO_2$.

FIG. 19.

A schematic representation of a system for the analysis of arterial blood flow velocity measurements is depicted.

FIG. 20.

A schematic representation of an apparatus for carrying out a method of the invention for determining the pulsatile vascular resistance is depicted.

DETAILED DESCRIPTION

Figure 19:
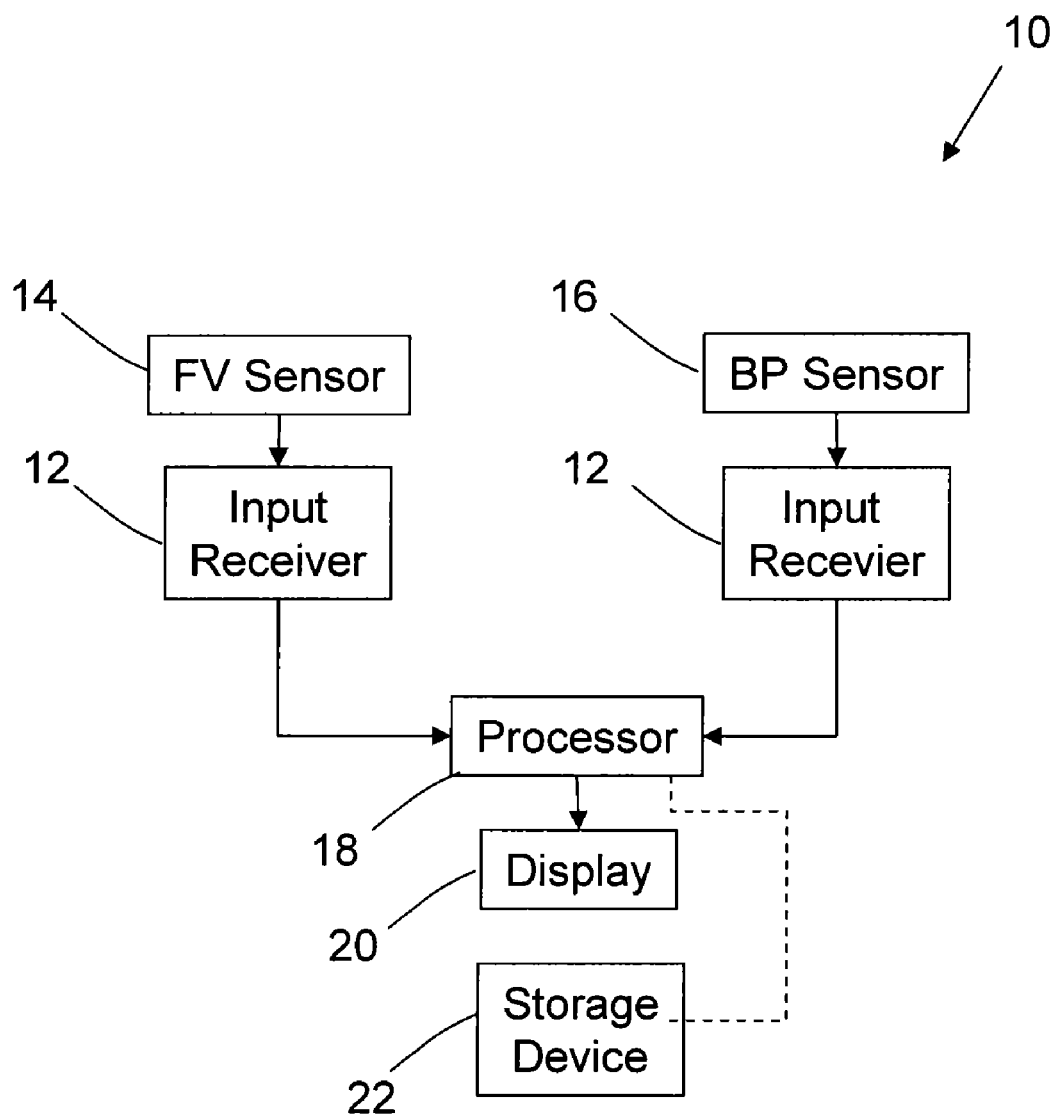

With reference to FIG. 19, the present invention includes a system for the analysis of arterial blood flow velocity measurements, system 10 includes means for receiving input signals 12 delivered by an arterial blood flow velocity (FV) sensor 14 and by an arterial blood pressure (BP) sensor 16. The system 10 further includes means for processing and outputting signals 18. The system further includes means for displaying 20 input and processed signals and/or means for storing recorded or displayed input or processed signals 22.

Figure 20:
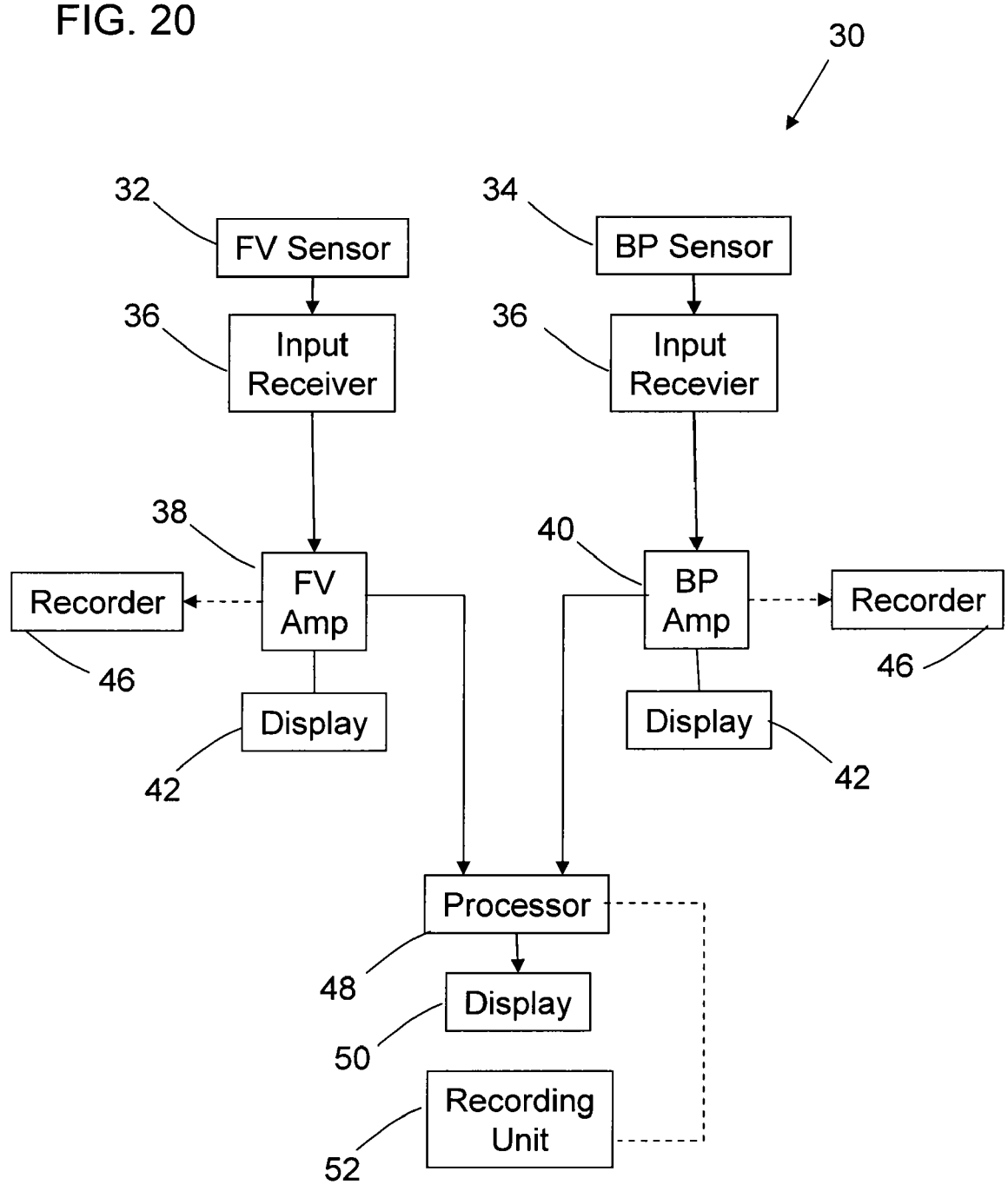

With reference to FIG. 20, the present invention also includes is an apparatus for carrying out a method of the invention for determining the pulsatile (apparent) vascular resistance, PaR or PFVM. Preferably, the apparatus 30 includes a sensor for continuously recording an arterial blood flow velocity (FV) signal 32 and a sensor for continuously recording an arterial blood pressure (BP) signal 34. The sensors are connected to means for receiving input signals 36, optionally further including a separate amplifier for FV, 38, and BP, 40, which amplifiers generate signals which can be displayed on a display unit 42 or recorded on a recording unit 46. The amplifiers are both connected to a processor 48 for performing signal analysis and calculation of the PaR or Pulse Flow Velocity Mismatch (PFVM). The amplifiers and the processor are connected to a display unit 50 or a recording unit 52 or both. In a specific embodiment, an apparatus of the invention includes a transcranial Doppler ultrasound device and/or a non-invasive continuous finger blood pressure monitor, such as a Finapres™ or Portapres™ device.

The apparatus of the invention can be a stand-alone apparatus, which has the features as described above. It is also possible that the features are incorporated into a module, which can be coupled to or inserted in conventional devices, which are used in the same environment. It would be possible to plug such a module into a device, which is used for monitoring patients in a hospital or surgery environment, such as the above-mentioned transcranial Doppler ultrasound devices, blood-pressure meters, devices for the control and monitoring of anaesthesia, etc.

EXAMPLES

The following examples illustrate the use of a system according to the invention as a diagnostic device. In Examples 1-6, BP signals were recorded using a Finapres™ device in conscious subjects or a indwelling catheter in the radial artery in anaesthetized subjects during carotid surgery. FV signals were recorded in both right and left middle cerebral arteries (MCA) in a human subject with Pioneer EME 2020 ultrasound equipment carrying a 2 MHz pulsed Doppler transducer. The Doppler probe was mounted over the squamous temporal bone using an elastic head band. The middle cerebral arteries (MCA's) were insonated at depths varying from 45 to 55 mm. The maximum flow velocities were used for display and analysis.

In Example 7 and 8 the experimental set-up for BTB (beat-to-beat) analysis of middle cerebral artery flow velocity and arterial blood pressure consisted of a Pioneer-EME 2-MHz Transcranial Doppler apparatus, an Omnipres blood pressure apparatus and an EEG recording system. The latter was a Dell computer with OSG-Brainlab 4.00 software enabling 32-channel data acquisition.

All subjects were supine. One ECG electrode was mounted on the back of the right shoulder the other on the chestwall in de midclavicular line over the left ninth or tenth intercostal space. Both ECG electrodes were fed directly into the EEG apparatus. A Spencer Technologies headframe was mounted on the patient's head in order to fix the probes of the TCD apparatus over the temporal windows. On both sides the middle cerebral artery was insonated at a depth of 50-54 mm and with a gate length of 10-11 mm. The gain was adjusted in order to obtain an optimal outline of the maximal flow velocity with respect to background noise. This so-called envelope was fed as analogue signal into the EEG apparatus. A finger cuff was mounted to the index finger of the patient's left hand. Arterial blood pressure was derived from this finger cuff by means of the Omnipres apparatus which enabled an analogue output to be fed in to the EEG apparatus.

Simultaneous recording of ECG, left and right middle cerebral artery flow velocity and arterial blood pressure was performed by analogue-to-digital conversion at a sample frequency of 250 Hz per channel. Data was stored on hard disc for later retrieval. Analysis was performed by extracting the data from hard disc (transforming the recorded Brainlab signals to an ASCII-file) and subsequently analysing the data within a Microsoft Excel spreadsheet environment.

Example 1

PFVM Analysis During During Deep Breathing

Deep breathing is a well accepted testing procedure for the autonomic nervous system. The large shifts in intrathoracic pressure resulting from the forced breathing activate baroceptors in the heart atria, in the aortic arch and in the carotid bodies. These baroceptors evoke changes in heart frequency synchronous with the respiratory phase. Inspiration (resulting in negative intrathoracic pressures) causes the heart beat frequency to rise whereas forced expiration (resulting in positive intrathoracic pressures) evokes a lowering of heart beat frequency (FIG. 3A).

The mean normalized pulsatile signals of ABP and MCA-FV may show a biphasic pattern (FIG. 3B). Calculation of the PFVM, however, results in a monophasic oscillating signal in counter-phase with the oscillation of heart beat frequency (FIG. 3C).

It is noteworthy that the PFVM decreases during forced inspiration and increases during forced expiration. Close analysis of the changes in heart beat frequency and PFVM indicate that PFVM is especially low during the first beat when the subject has shifted from inspiration to expiration and is highest when the subject shifts from expiration to inspiration.

When the interval between two heart beats is long (first few beats during expiration) the arterial blood pressure is allowed to decrease more during diastole. Since the body aims to keep cerebral blood flow as constant as possible this effect is counteracted by a decrease in PFVM, thus a decrease in pulsatile cerebrovascular resistance.

When the interval during two heart beats is short (first few beats during inspiration) the arterial blood pressure is still high when the next heart beat occurs. This would result in a higher cerebral blood flow, but this effect is antagonized by an increase in PFVM, thus an increase in pulsatile cerebrovascular resistance.

These effects together make that over time the cerebral blood flow and blood flow velocity show less respiratory fluctuations than does the ABP. Tentatively, the oscillation in PFVM manifesting itself during deep breathing indicates normal physiological intracranial vaso-reactivity, the absence of which may in future possibly prove to be a risk factor for cerebrovascular disease.

Figure 4B:
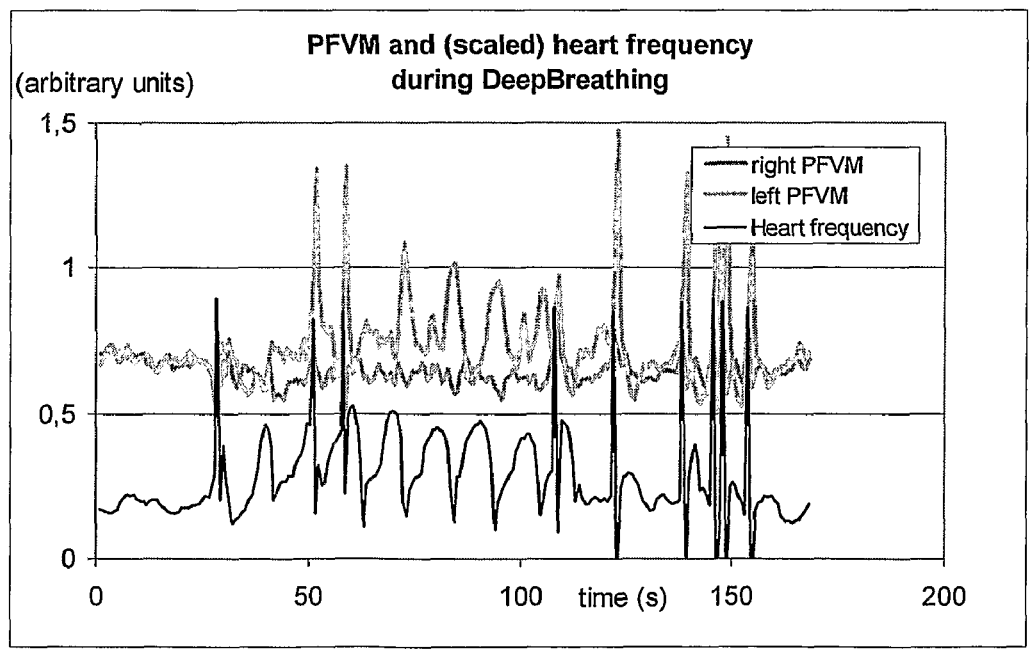

In a patient with a right sided carotid artery stenosis who was shown to have a decreased $CO_2$ reserve capacity on the right side, a marked difference in oscillation of the PFVM during deep breathing was found (FIG. 4A) which explained the differences in oscillation in overall MCA flow velocity observed between both middle cerebral arteries (FIG. 4B).

Example 2

PFVM Analysis During Hyperventilation

Figure 5A:
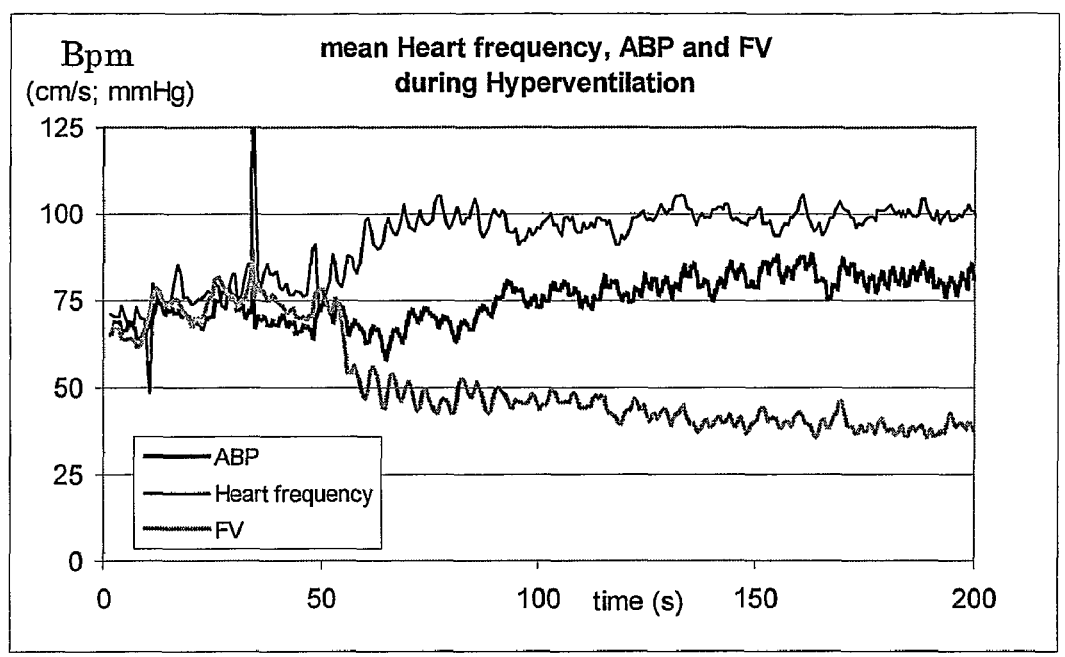
Figure 5:
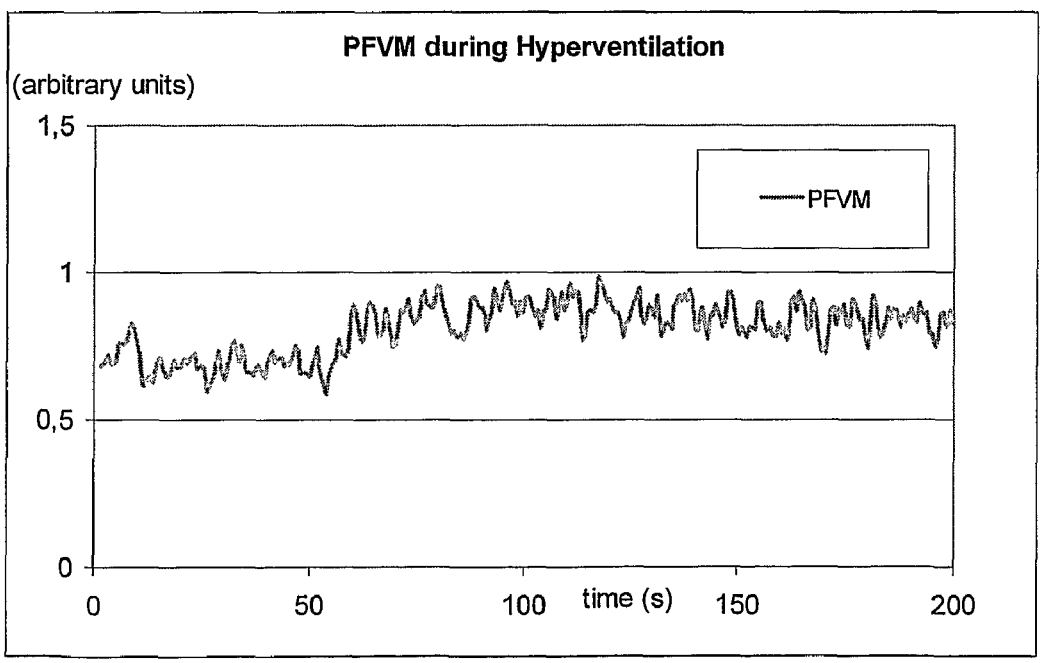

Hyperventilation may result in a significant lowering of the blood level of carbon dioxide. This may have its effect on intracranial as well as on extracranial blood vessels. High levels of carbon dioxide result in vasodilatation, whereas low levels of carbon dioxide induce vasoconstriction. FIG. 5A shows the MCA, BP and heart frequency analysis in a patient performing hyperventilation. During profound hyperventilation the calculated PFVM approaches 1, indicating a marked increase in pulsatile CVR (see FIG. 5B). Since calculation of the PFVM takes into account alterations in systemic ABP, the increase in PFVM can only be attributed to vasoconstriction of intracranial vessels and thus to the action of cerebral autoregulation.

Forced hyperventilation is a well known treatment for increased intracranial pressure, for instance in severe cerebral contusion. Therapeutic hyperventilation is usually adjusted with respect to the end tidal levels of carbon dioxide in exhaled gases. However, we now show that the PFVM is an alternative, possibly more suitable, parameter for optimization of therapeutic hyperventilation.

Example 3

PFVM analysis During Cross-Clamping and Clamp-Release

During cross clamping of the carotid artery for endarterectomy a drop in ipsilateral MCA-FV may occur. Often, the drop in pulsatility of the remaining MCA-FV signal is evident. It was observed that indeed the PFVM over the ipsilateral MCA may decrease somewhat, indicating a slight drop in pulsatile CVR (data not shown). On clamp release, one may expect a marked increase in blood supply to the circle of Willis, since a significant stenosis in the internal artery has now been removed. This increase in blood supply should be counteracted by an increase in cerebrovascular resistance to prevent high pressure levels reaching into the cerebral capillaries. Indeed, on clamp release the PFVM was found to increase dramatically. Tentatively, if the PFVM fails to show such a marked increase on clamp release this may correlate with a higher risk for postoperative hyperperfusion syndrome. This syndrome occurs in roughly 1% of all patients undergoing carotid endarterectomy. The CVR in these patients cannot adequately be increased in order to withstand the increase in cerebral perfusion pressure. High perfusion pressures reach the cerebral capillaries, resulting in the effusion of blood components with neurological deficit, epileptogenesis, intracranial haemorrhage and death as significant complications.

Example 4

PFVM Analysis During Mental Activity

Figure 6B:
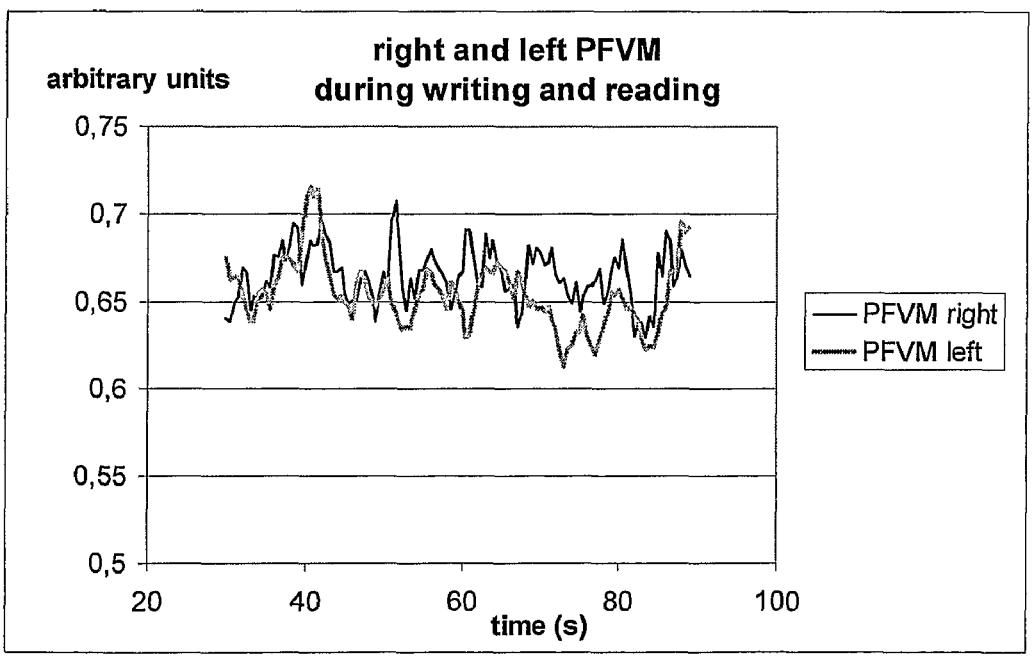

It is well known that mental activity may increase local cerebral blood flow. This can also be shown with TCD techniques. For instance, FIG. 6A shows the mean FV of the left versus the right MCA in a subject asked to copy words with his right index finger on a surface read from a text held in front of him (a typical test for left hemisphere function). FIG. 6B demonstrates the right and left PFVM under these conditions. Both figures are averages from 5 successive testing periods. From these figures it becomes clear that the mean MCA-FV on the side of the active (left) hemisphere may increase without marked changes in PFVM. Apparently, the PFVM is less sensitive for changes in local cerebral activity than is the mean MCA-FV. Tentatively, the PFVM is related more to the adaptation of CVR in response to marked changes in ABP than to local cerebral metabolism.

Example 5

PFVM Analysis During General Anaesthesia

Figure 7A:
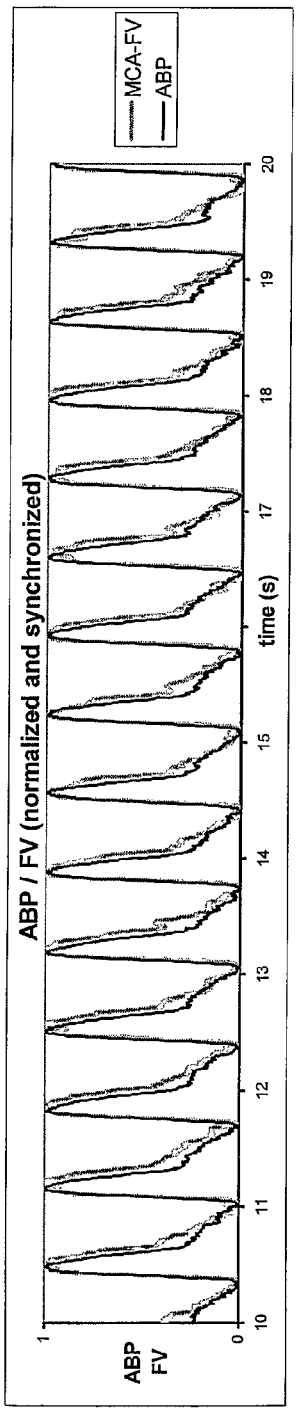
Figure 7B:
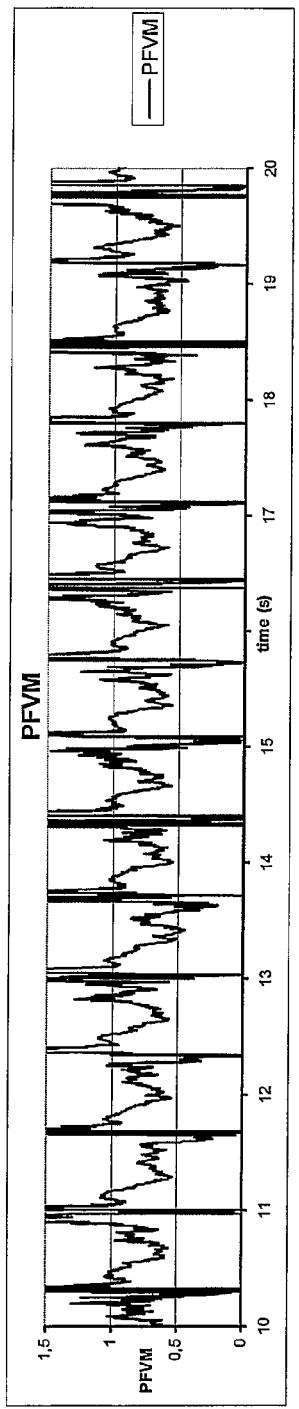
Figure 7C:
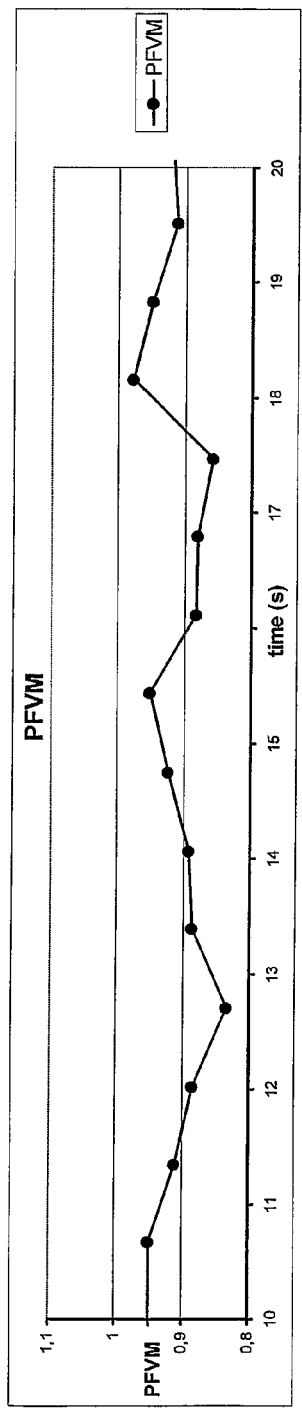

As mentioned before, under general anaesthesia the normalized pulsatile signals of ABP and MCA-FV match well, resulting in a PFVM close to 1. This is demonstrated by FIG. 7, displaying the superimposed and time shift corrected signals of normalized pulsatile ABP and MCA-FV during anaesthesia (FIG. 7A), as well as the calculated continuous PFVM (FIG. 7B) and PFVM per heart beat (FIG. 7C). Hypothetically, PFVM is correlated with the action of the autonomic nervous system. When the function of the autonomic nervous system is inhibited, as is the case during most forms of general anaesthesia, the Pulse Flow Velocity Mismatch is essentially equal to 1, which in fact means that there is little or no difference ("mismatch") between the mean normalized FV and BP.

Example 6

PFVM Analysis in Response to Medication

Since general anaesthesia has such a marked effect on the PFVM, it may also be inferred that other drugs with intracranial action can alter PFVM. The PFVM is conceivably controlled by various vaso-active substances released by intravascular nerve terminals. Thus, a system of the invention yielding the PFVM parameter is advantageously used to test the ability of known or new drugs to act on these vaso-active substances or their receptors (for instance, sumatriptan analogs).

Example 7

Calculation of PaR in a Clinical Setting: Carotid Dissection

A 47-year old woman, without prior medical history, was taken into hospital at 1:30 am after developing sensory disturbances on the right side of the tongue several hours earlier followed by a variable aphasia and right-sided hemiplegia shortly before hospital admission. At neurological examination she presented with an expressive aphasia and a right-sided hemiplegia involving the right side of the face and the right arm more than the right leg. Tendon reflexes were slightly increased on the right side of the body. The patient expressed some sensory disturbances at the right side of the face and the right arm. Blood pressure was 145/93 mmHg at a heart rate of 100 BPM. A CT scan of the cerebrum at hospital admission showed no abnormalities apart from an increased radiodensity of the distal part of the left carotid artery. Ultrasonographic investigation of the carotid arteries on the day of admission showed a echolucent filling of the left internal carotid artery resulting in a subtotal stenosis. Flow velocities over the left ICA were decreased to values lower than 30 cm/s systolic. An investigation of the intracranial arteries disclosed asymmetry of the flow signals over the two middle cerebral arteries with a pulsatility index (PI) on the left between 0.40 and 0.48, whereas values on the right varied from 0.69-0.73. The mean flow velocities were almost symmetrical. In addition, high antegrade flow velocities over the right anterior cerebral artery and a high retrograde flow velocity over the left anterior cerebral artery indicated right to left collateral flow via the anterior communicating artery. An MRI investigation on day 3 of hospital admission showed a stenosis of the internal carotid artery reaching into the carotid siphon confirming the diagnosis at ultrasonography.

On the day of hospital admission the patient underwent a combined study of ECG, TCD and continuous ABP.

The dissection of the left carotid artery will result in an increased inflow resistance to blood entering the circle of Willis via this artery. Consequently, a decrease of intra-arterial pressure will occur at the origin of the left middle cerebral artery which allows blood to flow in from other parts of the circle where the pressure is higher, for instance, from the basilar artery via de posterior communicating artery or from the contralateral carotid artery via the anterior communicating artery. In our patient collateral flow was mainly derived from a right-to-left shunting through the anterior communicating artery as demonstrated by TCD.

Depending on the flow resistance over the collateral vessels the resulting pressure at the origin of the middle cerebral artery may ideally reach normal values, usually the pressure will be lower than normal. In our patient the collateral flow was sufficient for obtaining symmetrical flow velocities over the MCA, but the pulse wave was dampened on the left side in comparison to the right, as shown by the lower pulsatility index on the left.

In response to the acute dissection our patient developed high blood pressures reaching levels of 150 over 95. On the unaffected, right side, these high pressures will result in a higher than normal pressure at the origin of the right MCA. Therefore, it was not unexpected that the maximal flow velocities over both MCA showed marked differences as demonstrated by the raw signals displayed in FIG. 8a.

On the unaffected right side the MCA flow velocities showed a high pulsatility with a rapid rise at pulse onset (upstroke) and a gradual tapering off during diastole. This diastolic phase shows a high frequency component hypothetically caused by a variable vasoconstriction within the MCA and its primary branches. On the left side, the upstroke of the MCA-FV is less rapid and the high frequency components in the diastolic phase are almost absent. Nevertheless the mean flow velocity for both sides is almost the same. During deep breathing (FIG. 8b.) the mean flow velocity over the right MCA decreased whereas that over the left remained largely unchanged. At rest, the BTB analysis of the mean flow velocities will show a relative symmetry between both MCA, as demonstrated in FIG. 9a. Therefore, although the pulsatile flow characteristics may be very different this may escape from our attention if only mean flow velocities are plotted, as is often the case in conventional TCD-machines set in monitoring mode.

Figure 9A:
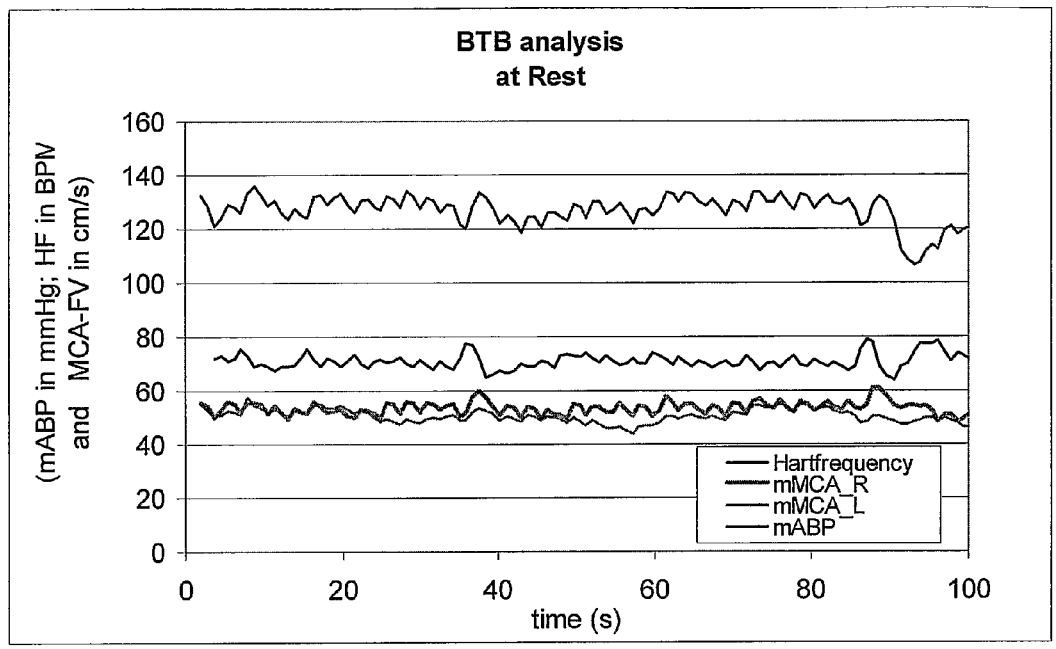
Figure 9B:
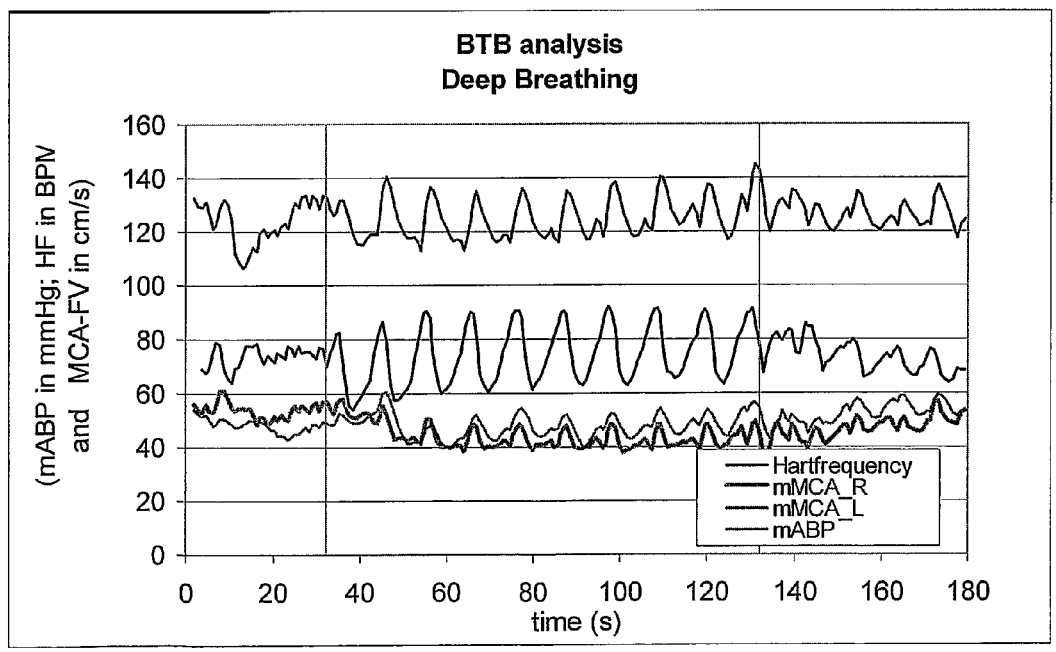
Figure 10A:
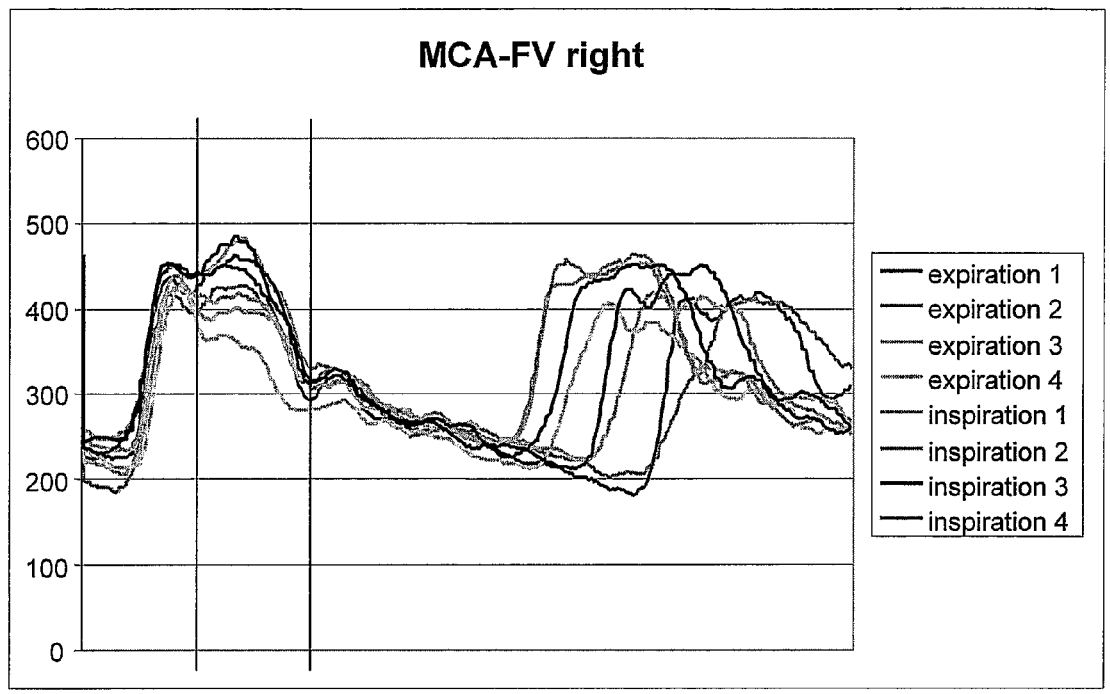
Figure 10B:
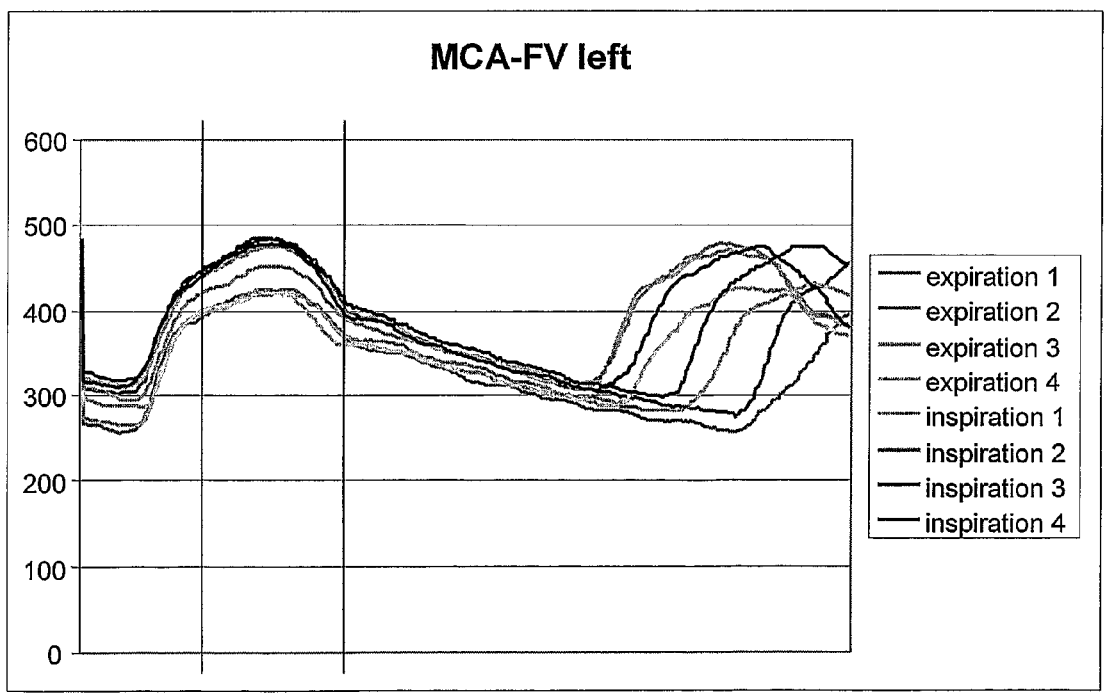
Figure 10C:
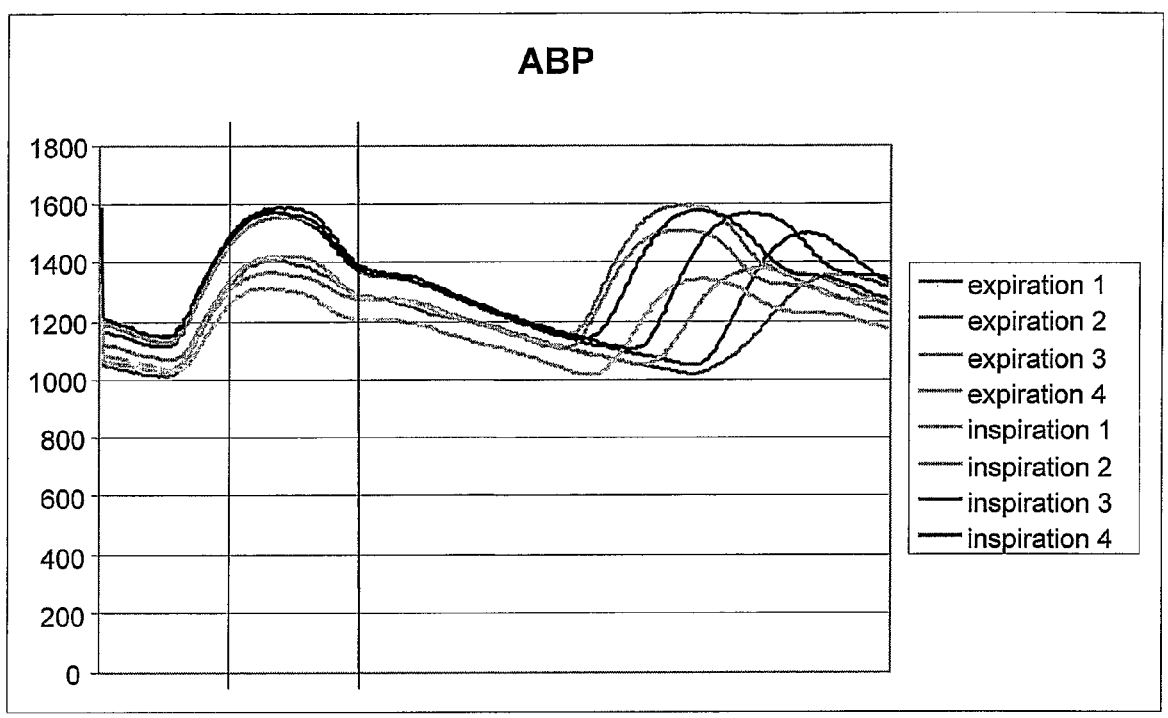

Now FIG. 9a shows that both signals are not completely identical: they differ in their frequency components: the right side contains middle frequency components related to the respiration at about 0.3 Hz, whereas the left side does not show these middle frequency components but instead shows low frequency components <0.03 Hz hypothetically related to fluctuations in metabolic activity and/or $CO_2$ levels within the MCA vascular territory. During deep breathing (FIG. 9a.) the respiratory fluctuations in flow velocity are accentuated and now become visible on the left side too. The mean flow velocity decreases for the right but remains largely unchanged on the left side. Due to deep breathing a marked respiratory arrhythmia becomes visible in the calculated heart frequency as well as a low frequency oscillation in the mABP. By averaging the information on ABP and MCA-FV for different phases of the respiratory cycle (as explained above) we can have a closer look at the pulsatile characteristics of both signals (FIG. 10a-c). FIG. 10c displays the averages over 3 similar heart cycles for different phases of the respiratory cycle. All signals are synchronised with respect to the QRS-complex of the ECG at t=0. Firstly, it becomes clear that there is a considerable respiratory arrhythmia during deep breathing. The HR in this patient varied from 60-90 BPM. HR increases during inspiration and decreases during expiration. This can be checked when we follow the graphs by colour code. Also, FIG. 10c. shows that during respiration there is a large variance in blood pressure: blood pressure is highest at end inspiration and lowest at end expiration. This variance in blood pressure leads only to a slight variance in MCA-FV, at least on the right side (FIG. 10a.). This figure shows that the flow velocity over the MCA is remarkably similar during diastole despite the differences in ABP. During systole the flow velocities seem more dependent on ABP: highest at end inspiration and lowest at end expiration. Clearly, there are differences in the regulation of CVR between the systolic and diastolic phase for the right MCA. The left MCA (FIG. 10b.), on the contrary, seems much more dependent of ABP: the flow velocities vary with the blood pressure during systole as well as diastole. Of course, after dissection of the left internal carotid artery this side has partially become dependent upon the right internal carotid artery due to right to left shunting via the anterior communicating artery.

Figure 11A:
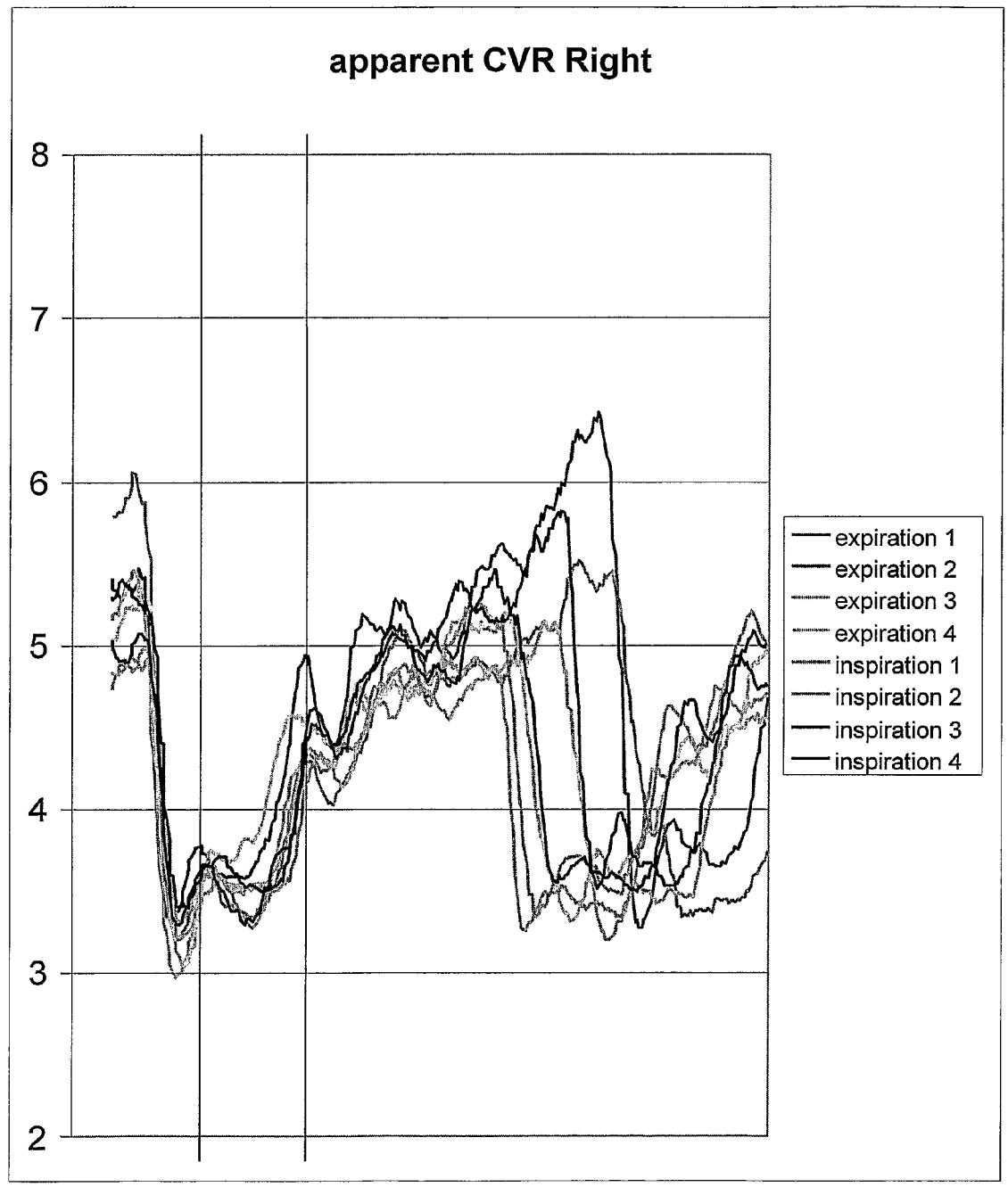
Figure 11B:
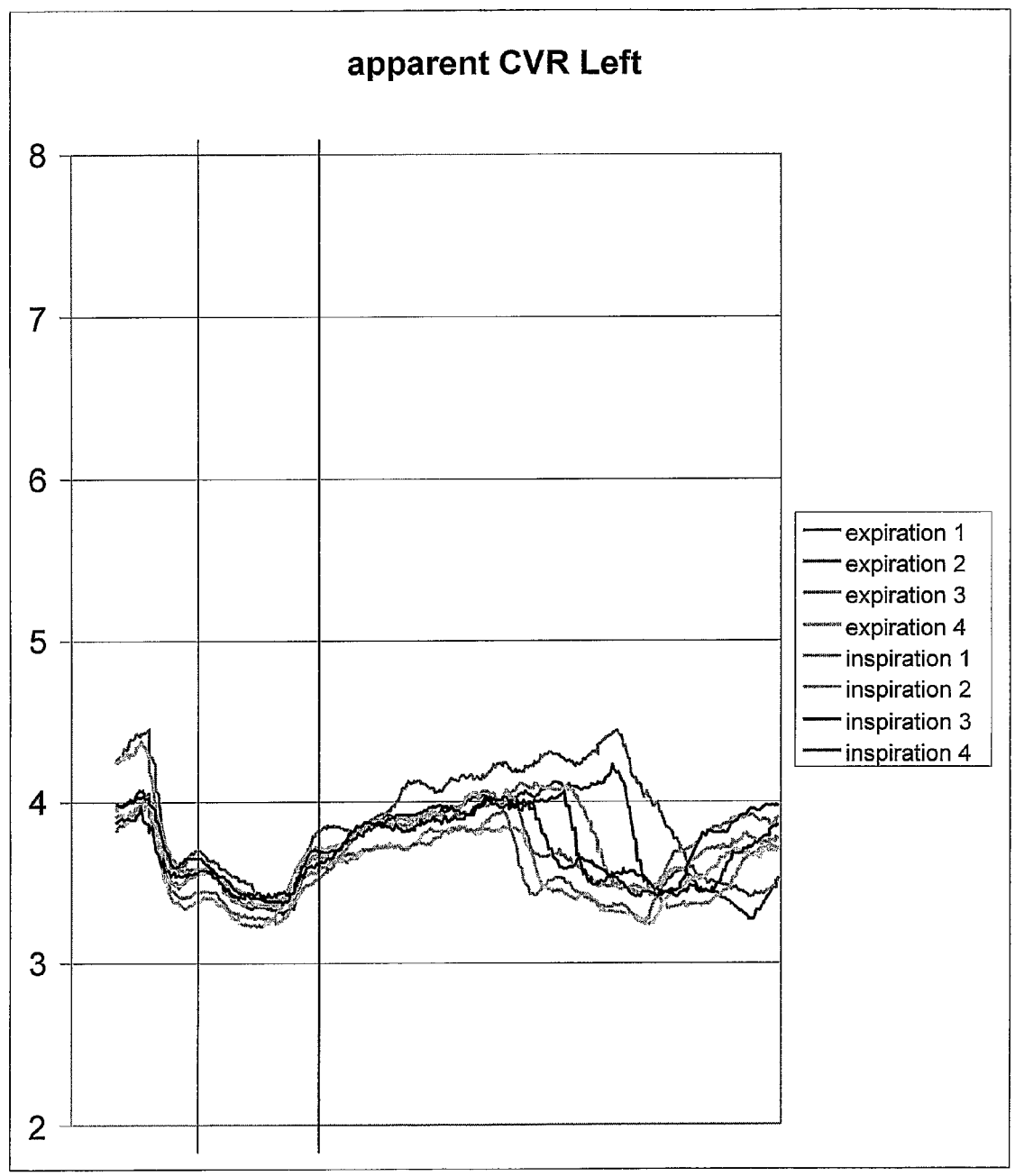

If we calculate the apparent CVR, by making use of formula (6) above, we can better illustrate the variation in CVR during one heart cycle. FIG. 11a shows the results for the right MCA, FIG. 11b for the left after synchronising the FV and ABP signals with respect to stroke onset. Since stroke onset is later for ABP than for MCA-FV the calculated aCVR is plotted with approximately 50 ms time delay. The apparent CVR is smaller during systole than during diastole. Within the time frame of 1 heartbeat the variation in aCVR is ascribed to the pulsatile variation in MCA cross-sectional area. A small diameter during systole will give a rise in blood flow velocity and thus a lowering of the aCVR. A wider diameter during diastole will give a relatively lower blood flow velocity and thus an increase in aCVR. Now the variability of aCVR during one heart cycle can be expressed relative to the long-term average mCVR (derived from formula 4) by applying formula (11). This will result in the so-called PaR. Comparing FIGS. 11a and b illustrates the dramatic difference in aCVR between the right and left side. Especially during diastole, aCVR reaches higher values on the right side than on the left. This can be taken to indicate that there is more variation in MCA diameter on the right than on the left side: the signal over the left MCA is less pulsatile. For diastole the aCVR of both sides is rather similar.

Figure 12A:
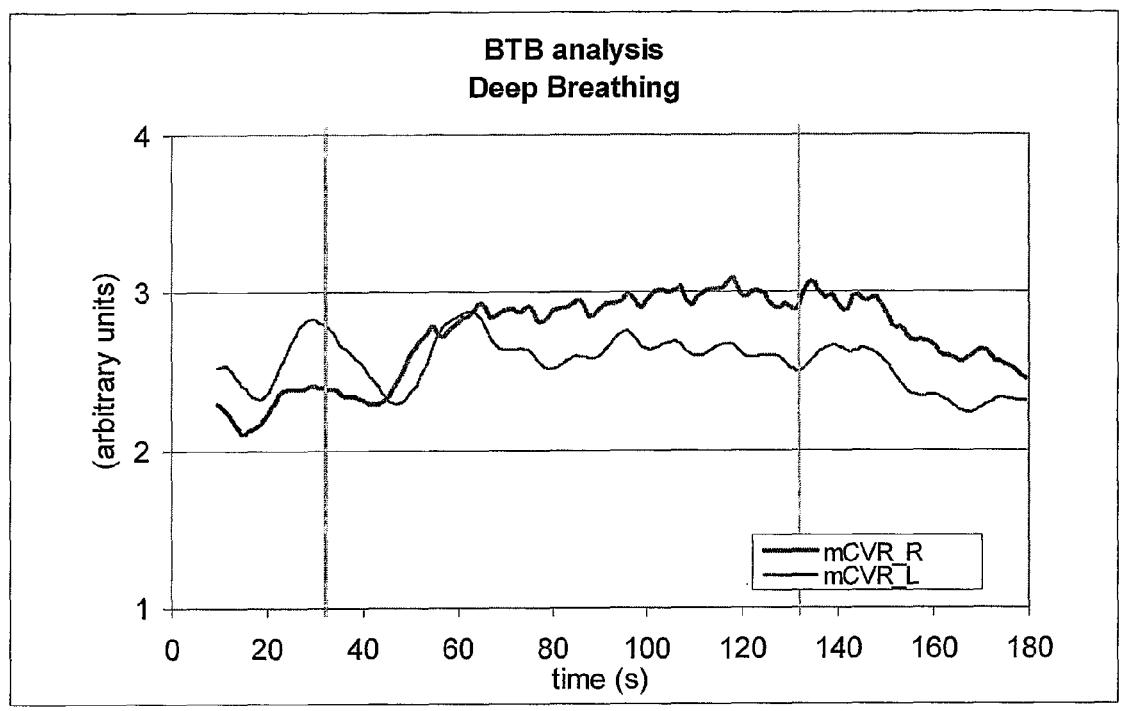
Figure 12B:
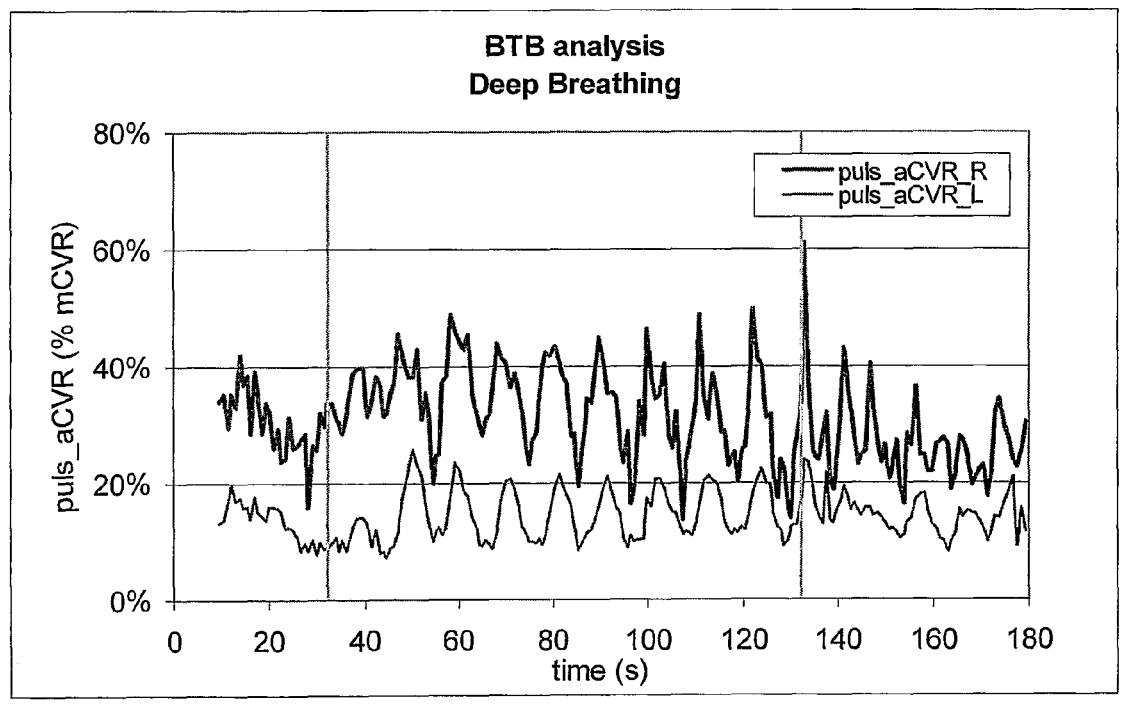

In FIG. 12a we have plotted the mCVR and in FIG. 12b the PaR as a function of time. From FIG. 12a it becomes clear that the mCVR follows the low frequency changes in CVR already visible in FIG. 9b. Vertical bars indicate the period of deep breathing. On the right side the lowering of the blood $pCO2$ results in vasoconstriction and thus in a decrease of MCA-FV. Since the mABP remains largely unchanged the calculated mCVR will increase as is clearly demonstrated in FIG. 12a. Also, the figure shows that there is far less change in mCVR for the left side. In this sample, the mCVR's are obtained by taking the average over 10 successive heart beats (in fact, over the present and 9 previous heart cycles). This will cause a low frequency filtering with a cut off frequency somewhat dependent on heart frequency. Despite this filtering there is a clear time lag visible between the onset of deep breathing and the increase in mCVR as well as between the increase in mCVR in right compared to left signal. This is in agreement with the raw signal (FIG. 9a).

It should be emphasised that mCVR is expressed in arbitrary units. mCVR depends on the mean MCA diameter, on the angle of insonation and on the possible attenuation of the blood pressure signal on its way to the circle of Willis. The interpretation of mCVR is therefore as ambiguous as of MCA-FV alone. In our patient, the mCVR seems slightly higher on the left than on de right side due to the extra resistance proximal to the left MCA caused by the dissection of the internal carotid artery. The pressure at the origin of the middle cerebral artery will therefore differ more from the measured systemic ABP on the left than on the right side. The calculation of mCVR is performed as if the systemic ABP is identical on both sides. Thus, in the case of a stenosis proximal to the MCA, the mCVR will be higher on the side of the stenosis, which is of course contra-intuitive if one wishes to use mCVR as a parameter describing the hemodynamic state of the cerebral tissue distal to the site of insonation. mCVR does act in a predictable way when vasoconstriction occurs within the cerebral arterioles, for instance during hyperventilation as demonstrated by FIG. 5a. But during vasospasm, on the contrary, the high MCA flow velocities will result in an apparently low mCVR, again a non-informative finding.

FIG. 12b shows the PaR during deep breathing. Although the mean MCA-FV's were rather the same and therefore the mCVR are within the same range, there is a marked difference between both signals with respect to the PaR. The PaR is much larger on the right than on the left side. This is fully compatible with the findings in FIGS. 11a and b comparing the aCVR during different phases of the respiratory cycle. The PaR numerically expresses the difference in flow velocity profile between both MCA's that was so obvious on visual inspection (FIG. 8).

The PaR indicates the difference between systolic and diastolic aCVR expressed as a percentage of mCVR. FIG. 12b demonstrates how different both MCA are with respect to their pulsatile characteristics: on the left side there is only a 10-15% difference between the systolic and diastolic aCVR, whereas on the right side this difference reaches values of 25-35%. Apparently, the pulsatile variation of the MCA vessel diameter on the right side is larger than on the left, resulting in a larger pulsatile resistance to the pressure wave at the origin of the right MCA than on the left.

Comparing FIGS. 12a and b shows that the timing of changes in these parameters can be quite independent: the first respiratory fluctuations in PaR occur before the onset of mCVR increase. Furthermore, the frequency content is quite different for both signals: large fluctuations in PaR due to respiration are far less obvious in the mCVR signal. The filtering of the mCVR signal can only partly account for this.

Figure 13:
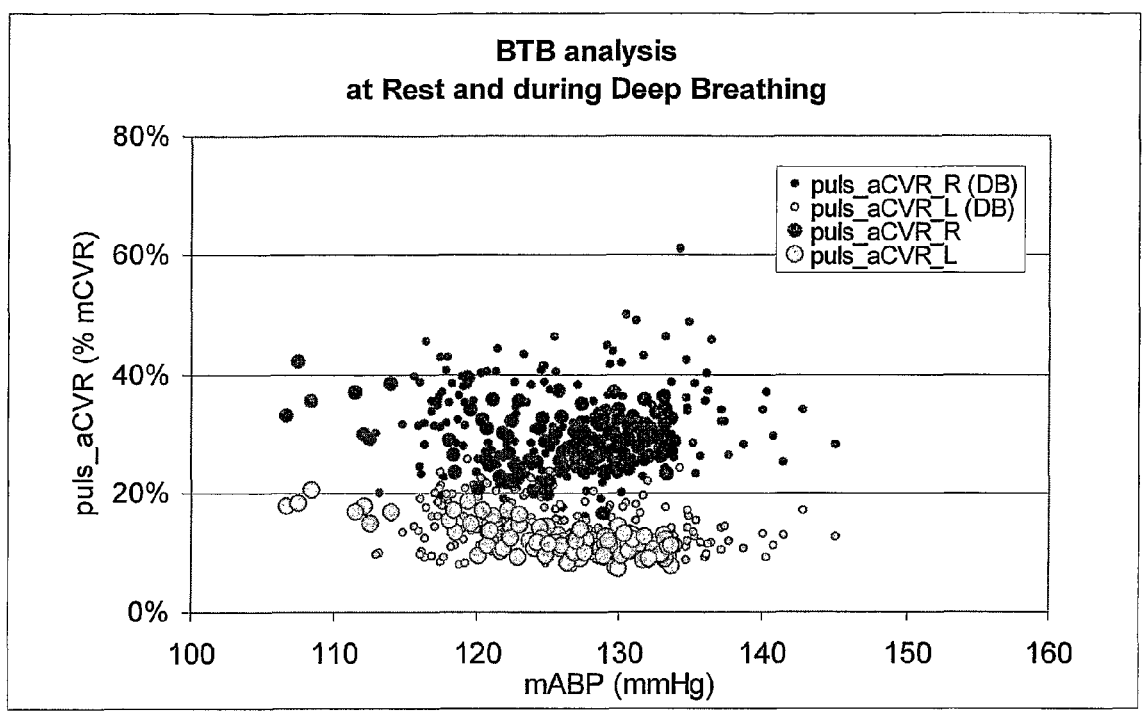

It is important to realise that, in contrast to mCVR, PaR can safely be compared between right and left MCA's. PaR is a unitless parameter and it is not influenced by the angle of insonation nor by differences in effective ABP at the origin of the MCA between both sides. As put forward earlier, the interpretation of PaR can be enhanced by plotting it in a xy-graph as a function of mABP (and/or $ETCO_2$, not illustrated). FIG. 13 displays a plot of PaR versus mABP. Data obtained from the patient at rest (large dots) as well as during deep breathing (small dots) are combined in one plot to provide insight in the variation within these parameters. At similar mABP's both MCA's clearly differ with respect to their PaR. The PaR on the right side is much higher than on the left. Furthermore, at increasing mABP, the PaR on the left side tends to decrease (approaching the end of the autoregulatory range), whereas that on the right side remains roughly the same. During deep breathing there is a larger variation of mABP that results in a larger scatter of data points. The values of PaR are driven by respiration and attain higher values on both sides.

From plots as FIG. 13, the clinician may deduce in what direction to influence mABP in order to improve PaR (shifting it away from baseline). A lower mABP will increase PaR for the left MCA while leaving that for the right rather unchanged. An increase in PaR will indicate more pulsatile variation in MCA diameter and thus more 'freedom of control' for cerebral autoregulation.

Example 8

Calculation of PaR in a Clinical Setting: Hemiplegic Migraine

A 52-year old woman with a history of lumbar disc surgery and hysterectomy who had been diagnosed with diabetes mellitus type II and hypercholesterolemia, was presented to the neurologist with acute onset of left sided hemiparesis, dysarthria and headache. This was the third episode with similar complaints. Extensive laboratory and neuroradiological investigation during two prior episodes was unremarkable apart from known diabetes and hypercholestrolemia. Repeated MRI and CT scanning of the cerebrum were normal. Standard Duplex investigation of the carotid arteries and TCD investigation of the intracranial cerebral arteries was unremarkable during prior visits to our department. She was seen for a neurovascular examination 2 days after symptom onset. The recurrent attacks with hemiparesis and headache were diagnosed as hemiplegic migraine. Within one week she spontaneously became symptom-free. A control visit for neurovascular exam was arranged 3 months later.

Figure 14A:
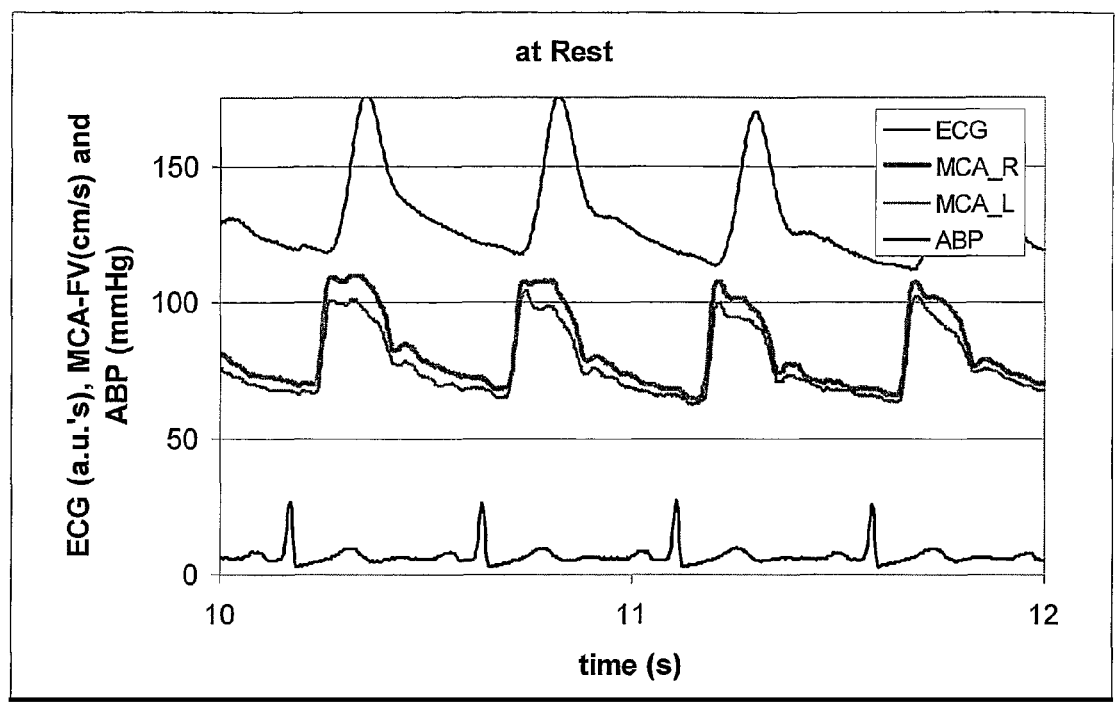
Figure 14B:
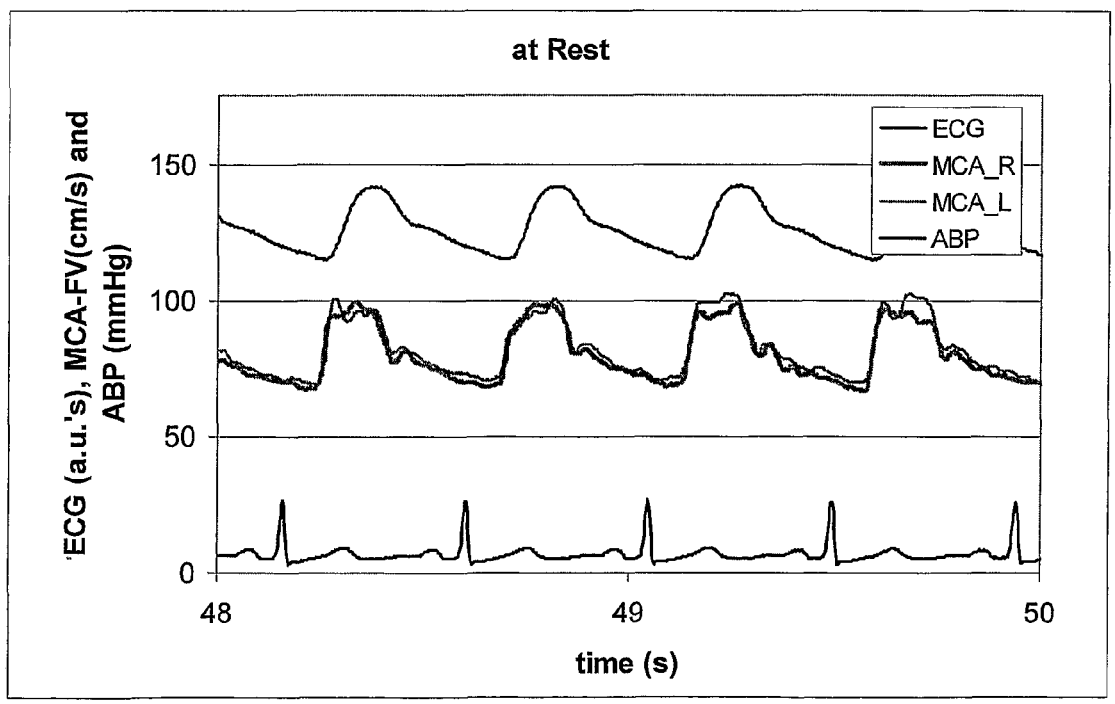
Figure 15A:
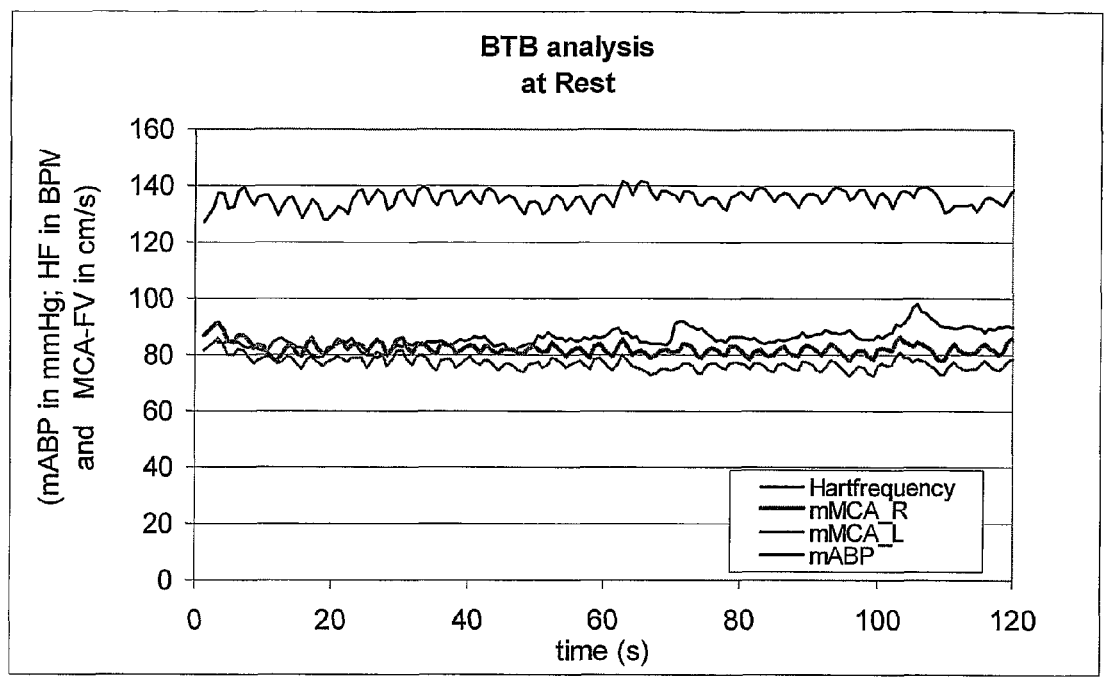
Figure 15:
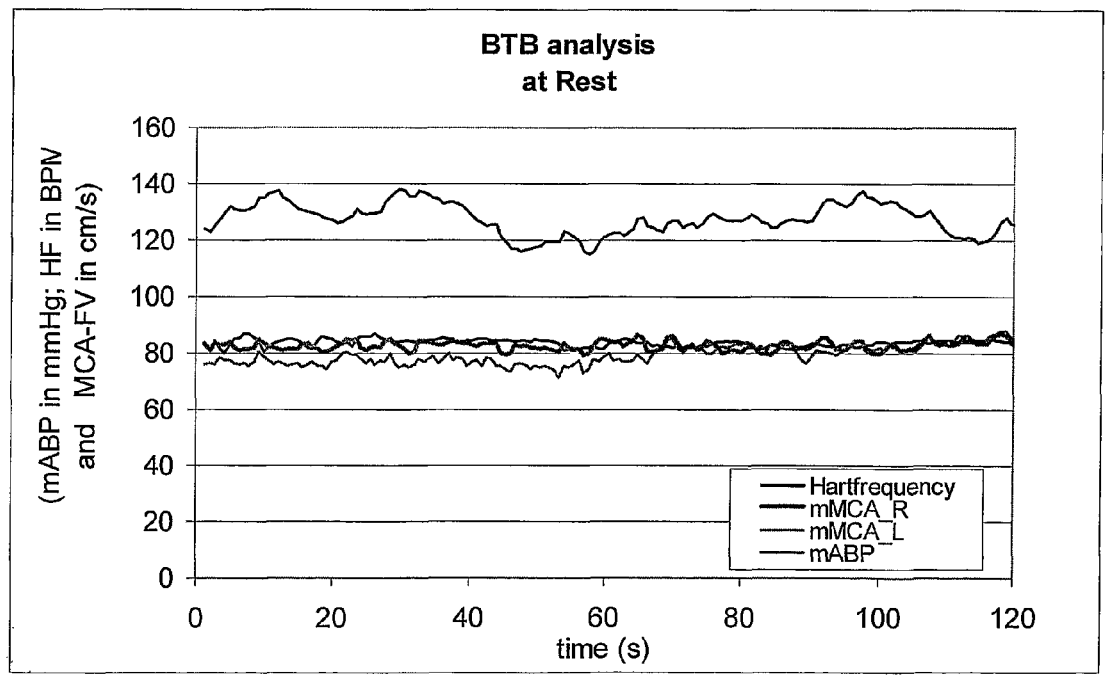
Figure 16:
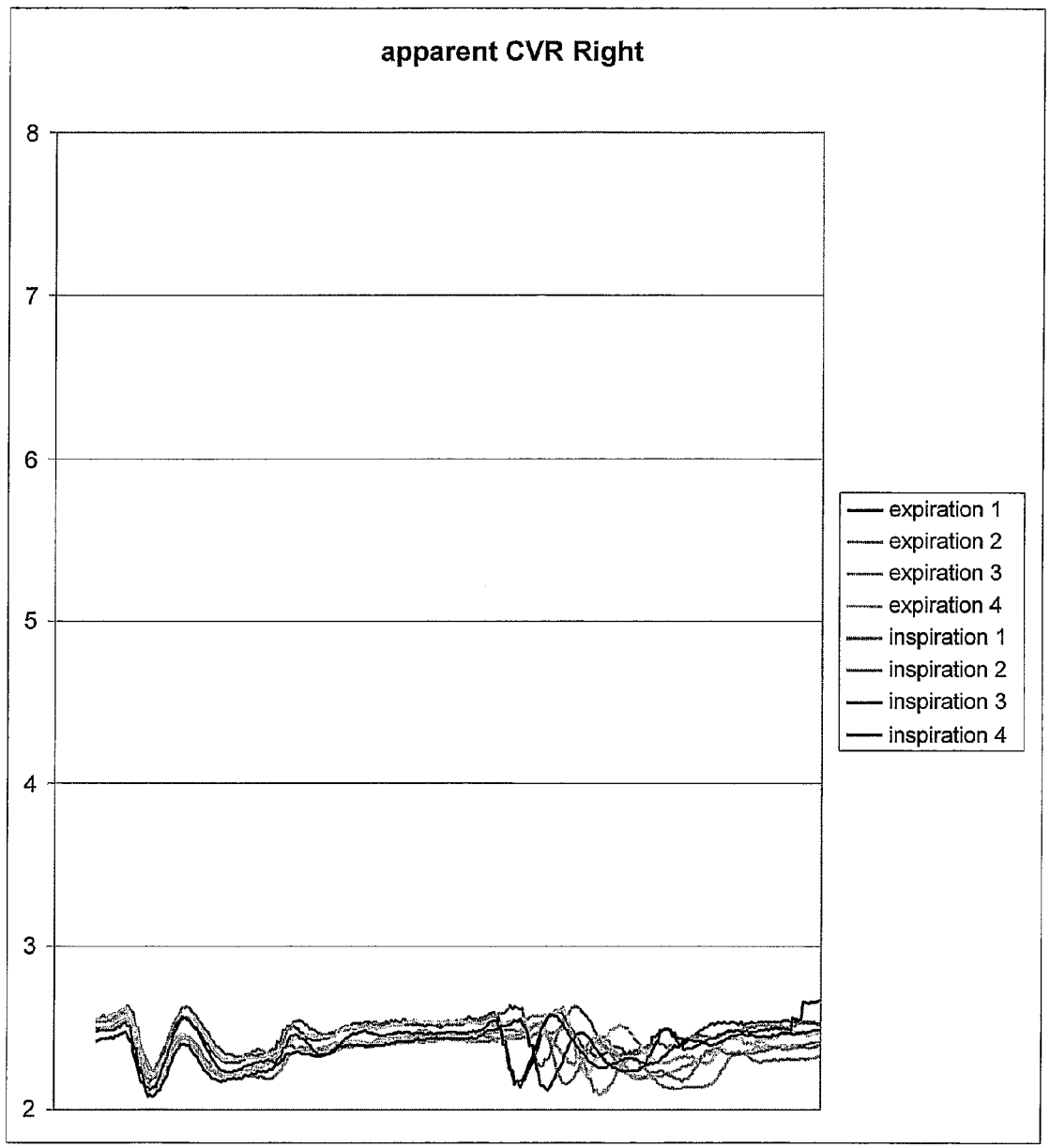
Figure 17:
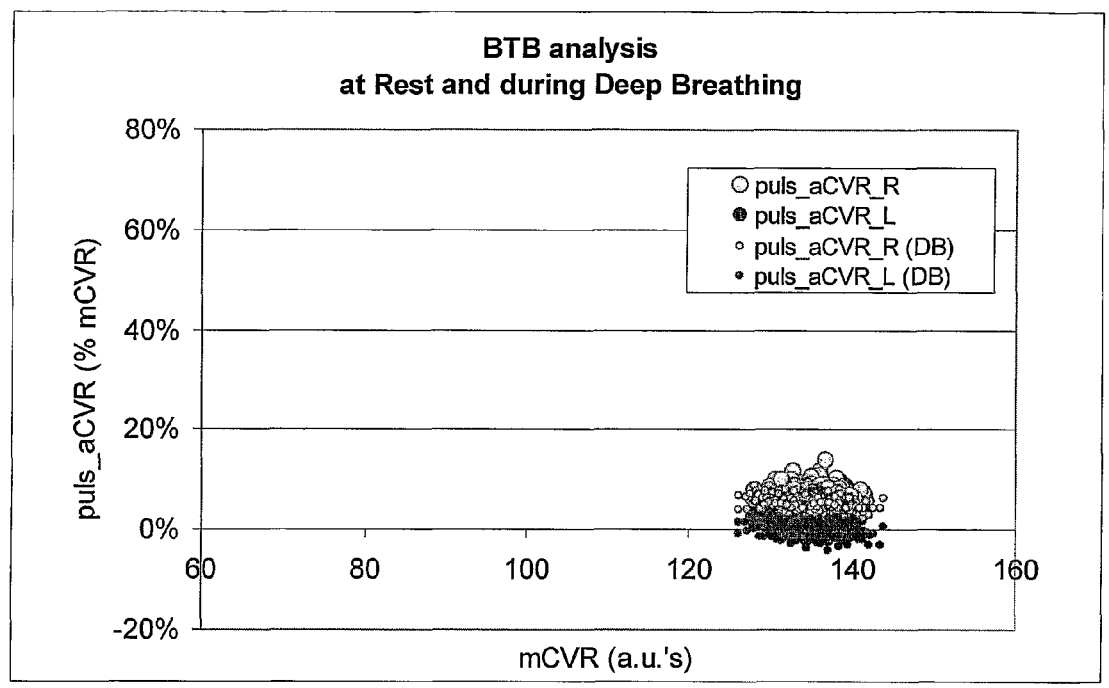
Figure 17B:
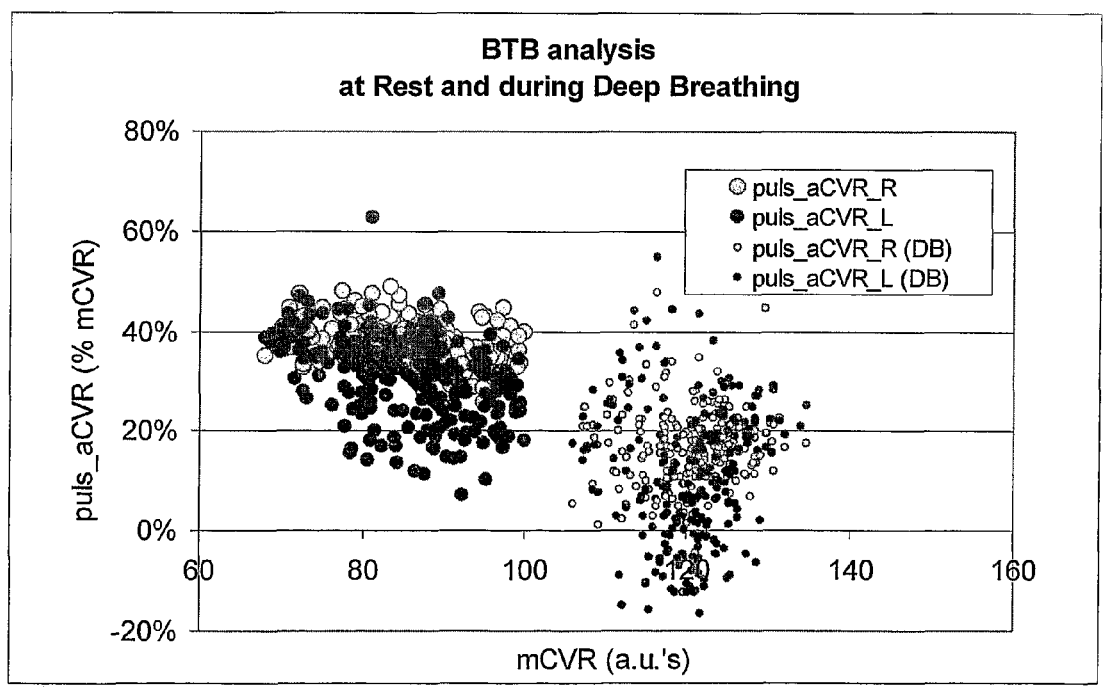

FIG. 14 shows raw data of the patient's ECG, ABP and MCA-FV when experiencing symptoms (FIG. 14a) and when symptom free (FIG. 14b). Most striking is the difference in the ABP signal. The ABP signal during symptoms was much more pulsatile than when the patient was symptom-free. Furthermore, there was a slight difference in MCA-FV's during symptoms, the right MCA showing slightly higher flow velocities than the right, that was no longer there when the patient became symptom-free. FIG. 15 shows the BTB analysis of the supine patient with normal ventilation while experiencing symptoms (FIG. 15a) and while symptom-free (FIG. 15b). Note the marked difference in frequency content of the ABP signal: in FIG. 15a the mABP signal displays a clear respiratory variation, whereas in FIG. 8b the respiratory fluctuation is less marked and a low frequency variation emerges. Heart beat frequency is similar for both conditions. Both MCA-FV's are distinctly different in FIG. 15a but almost co-incided in FIG. 15b. In 15a there is a clear respiratory fluctuation of both MCA-FVs in phase with the blood pressure, whereas this respiratory fluctuation is absent in FIG. 15b. FIG. 16 illustrates the apparent CVR for different respiratory phases during deep breathing. There is remarkably little difference between systolic and diastolic aCVR. The PaR will be close to zero. This is shown in FIG. 17a. Data were plotted for normoventilation (large dots) as well as deep breathing (small dots). Despite a drop in $ETCO_2$ from 3.8 down to 2.8 there was no marked change in MABP, nor in PaR. When the same tests were repeated during the symptom-free period puls_CVR was larger on both sides and, at a smaller drop in $ETCO_2$, from 4.7 to 4.2 there was a clear increase in mABP and decrease in PaR. What can be learned from this patient with an attack of hemiplegic migraine? The low PaR during the attack suggests that at rest there is little variation in MCA cross-sectional area: the aCVR during systole is almost equal to that during diastole. This suggests that the MCA are either maximally dilated or maximally vasoconstricted. Because from FIG. 17a we can deduce that PaR (slightly) increases at lower values for mABP we can conclude that the latter is the case. From the unchanged PaR during a marked reduction in $ETCO_2$ it can be inferred that the cerebral arterioles cannot or can no further vasoconstrict. During the symptom-free period PaR is larger and shows more variation in response to deep breathing (FIG. 17b). If the two graphs 17a and 17b were superimposed the relation between mABP and PaR would be no different during the period with symptoms compared to the period without: is migraine really a disease of the cerebral vessels alone or is it more a disease of systemic vascular control (and thus ABP) shifting cerebral vascular control to the limits of cerebral autoregulation?

Example 9

User Friendly Displays

Figure 18A:
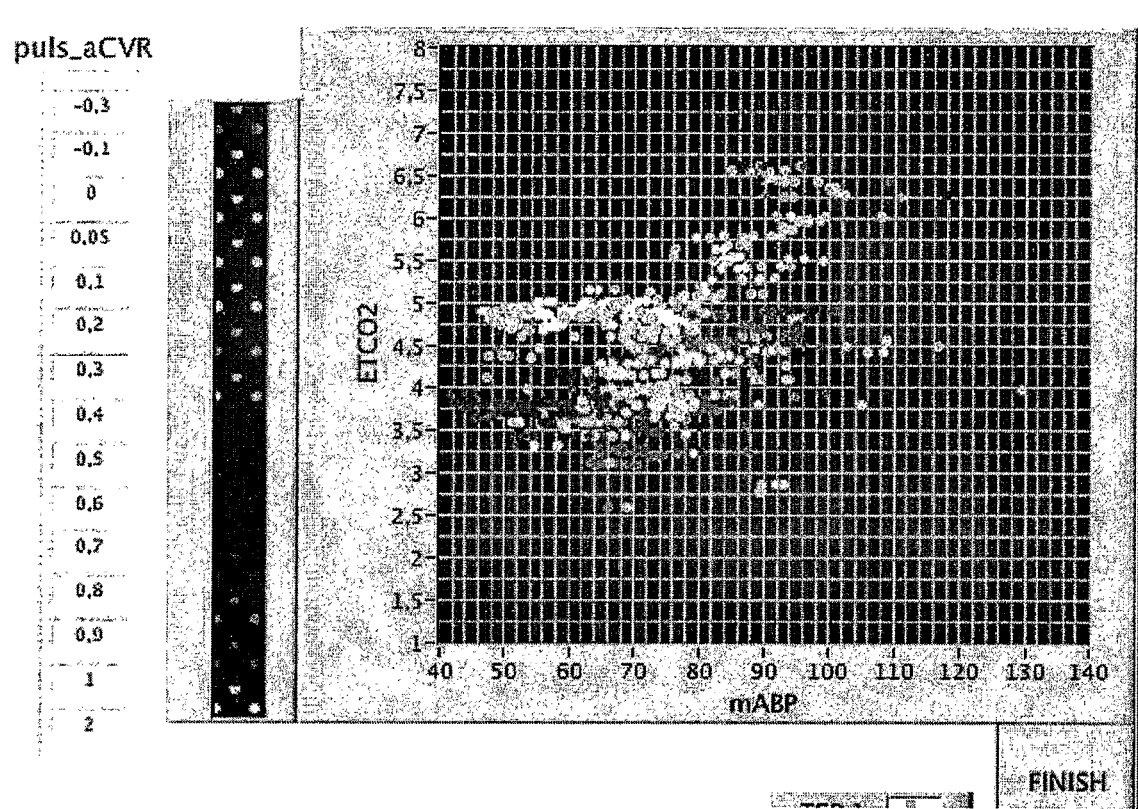
Figure 18B:
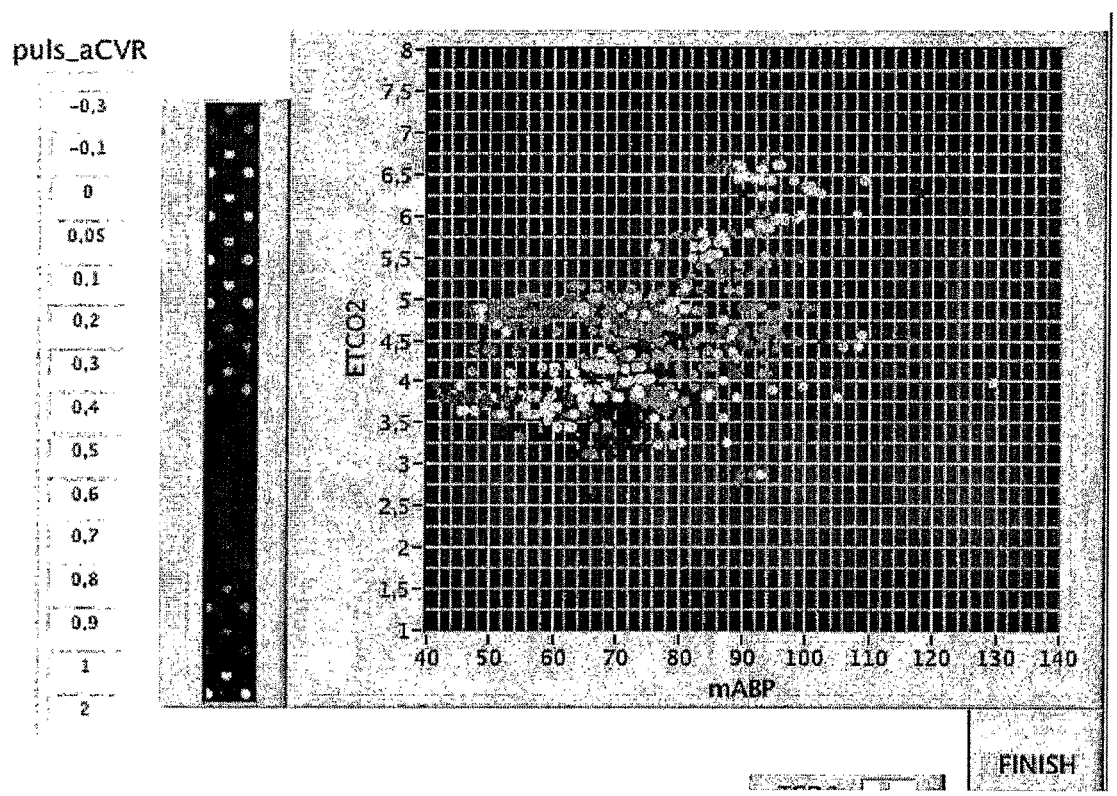

The two examples of Example 7 and Example 8, above, allow to demonstrate how new insights can be obtained about a patient's neurovascular condition by mathematically combining continuous signals derived from the TCD and ABP apparatus. PaR, especially when plotted as a function of MABP and/or ETCO2, is the most promising candidate parameter for neurovascular monitoring at the bed side. In the ICU-patient the optimal blood supply to the brain depends on an optimal choice of breathing parameters and blood pressure control together with, when indicated, therapeutic measures reducing intracranial pressure. This choice needs to be adjusted and re-adjusted for each patient individually. The on-line analysis of TCD and ABP combined with a user-friendly presentation to the clinician can in future be superior to any other technique in clinical decision-making at the bed-side for patients with a threatened blood supply to the brain. An example of what such a user friendly display would look like is provided in FIG. 18 (see legend for details). Here PaR has been colour coded prior to plotting as a function of MABP and ETCO2. Without going into detail the graph shows boundaries to combinations of mABP and ETCO2 for which PaR is normal (green colours), decreased (orange and red dots) or elevated (blue and pink dots). Note that every dot represents one single heart beat.

Acknowledgements

Clinical data of both patients of Example 7 and 8 was kindly provided by dr. J. W. Snoek (case 1) and dr. R. J. O. vd. Ploeg (case 2), both neurologist at the Martini Ziekenhuis in Groningen.

The invention claimed is:

1. A system for the analysis of arterial blood flow velocity measurements comprising means for receiving input signals delivered by an arterial blood flow velocity (FV) sensor and by an arterial blood pressure (BP) sensor, wherein said FV and BP signals are recorded simultaneously and continuously, further comprising means for processing and outputting signals, wherein said processing comprises:
   synchronization of both signals at start upstroke,
   a beat-to-beat analysis of the signals, whereby the pulsatile vascular resistance is calculated from the difference in relationship between FV and BP signals during systole compared to diastole.

2. A system according to claim 1 which further optionally comprises averaging to avoid respiratory effects; and wherein the calculated pulsatile vascular resistance is the Pulsatile apparent Resistance (PaR).

3. A system according to claim 2, which comprises:
   averaging the values for FV and BP over the systolic part or diastolic part of each heart cycle;
   calculating the difference between the diastolic vascular resistance and the systolic vascular resistance;
   determining the mean vascular resistance over a number of successive heartbeats, preferably ten or more; and
   determining the PaR as the ratio between this difference and the mean vascular resistance.

4. A system according claim 1 wherein the calculated pulsatile vascular resistance is the Pulse Flow Velocity Mismatch (PFVM).

5. A system according to claim 4 which comprises:
   normalizing said FV and BP signal with the minimal diastolic flow velocity or blood pressure set at 0 and the maximal systolic flow velocity or blood pressure set at 1;
   calculating the mean normalized FV and the mean normalized BP over a time period in between two successive heart beats; and
   determining the ratio between the mean normalized FV signal and the mean normalized BP signal (=PFVM).

6. A system according to claim 1, further comprising means for displaying input and processed signals and/or means for storing recorded or displayed input or processed signals.

7. A system according to claim 1, wherein said arterial blood flow velocity (FV) sensor detects the middle cerebral artery (MCA) flow velocity, preferably using transcranial Doppler technology.

8. A system according to claim 1, wherein said BP sensor comprises an intravascular catheter.

9. A system according to claim 1, wherein said BP sensor comprises a non-invasive sensor, preferably a non-invasive continuous finger blood pressure monitor.

10. Method for determining pulsatile vascular resistance (PVR), preferably pulsatile vascular cerebrovascular resistance, said method comprising the steps of:
    recording an arterial blood flow velocity (FV) signal and an arterial blood pressure (BP) signal, wherein said FV and BP signals are recorded simultaneously and continuously;
    synchronizing said FV and BP signal at start-upstroke;
    optionally averaging said signals to avoid respiratory effects; and
    calculating with a processing device the pulsatile vascular resistance in a beat-to-beat analysis of the signals, from the difference in relationship between FV and BP signals during systole compared to diastole.

11. Method according to claim 10 further comprising, diagnosing or monitoring a subject using the pulsatile vascular resistance.

12. Method according to claim 10 further comprising, diagnosing or monitoring a vascular disease or malfunction related to abnormal vascular resistance, preferably cerebrovascular resistance, or of elevated intracranial pressure using the pulsatile vascular resistance.

13. Method according to claim 10 in which the pulsatile apparent resistance (PaR), preferably cerebrovascular PaR, is calculated, said method comprising the steps of:
    averaging the values for FV and BP over the systolic part or diastolic part of each heart cycle;
    calculating the difference between the diastolic vascular resistance and the systolic vascular resistance;
    determining the mean vascular resistance over a number of successive heartbeats, preferably ten or more; and
    determining the PaR as the ratio between this difference and the mean vascular resistance.

14. Method according to claim 10, in which the Pulse Flow Velocity Mismatch (PFVM), preferably cerebrovascular PFVM, is calculated, said method comprising the steps of:
    normalizing said FV and BP signal with the minimal diastolic flow velocity or blood pressure set at 0 and the maximal systolic flow velocity or blood pressure set at 1;
    calculating the mean normalized FV and the mean normalized BP per time unit; and
    determining the ratio between the mean normalized FV signal and the mean normalized BP signal.

15. Apparatus for performing the method of claim 10, comprising a sensor for continuously recording an arterial blood flow velocity (FV) signal and a sensor for continuously recording an arterial blood pressure (BP) signal, the sensors being connected to means for receiving input signals, further comprising a separate amplifier for FV and BP, which amplifiers generate signals which can be displayed on a display unit or recorded on a recording unit, said amplifiers both connected to a processor for performing signal analysis and calculation of the Pulsatile apparent Resistance (PaR) or Pulse Flow Velocity Mismatch (PFVM), said amplifiers and said processor being connected to a display unit or a recording unit or both.

16. Apparatus according to claim 15, comprising a transcranial Doppler ultrasound device and/or a non-invasive continuous finger blood pressure monitor.

17. Method according to claim 10, wherein the calculation is performed by a module for calculation of the pulsatile vascular resistance, said module being connected to apparatuses that measure blood flow velocity and blood pressure.

* * * * *